US012661199B2

(12) United States Patent
Shen et al.

(10) Patent No.: US 12,661,199 B2
(45) Date of Patent: Jun. 23, 2026

(54) SURGICAL ROBOT SYSTEM

(71) Applicants: JROBOTICS INC, Irvine, CA (US); Bifeng Shen, Shanghai (CN)

(72) Inventors: Bifeng Shen, Shanghai (CN); Jiong Hong, Shanghai (CN)

(73) Assignees: JROBOTICS INC, Shanghai (CN); Bifeng Shen, Irvine, CA (US)

( * ) Notice: Subject to any disclaimer, the term of this patent is extended or adjusted under 35 U.S.C. 154(b) by 386 days.

(21) Appl. No.: 18/251,145

(22) PCT Filed: Aug. 9, 2022

(86) PCT No.: PCT/CN2022/111249
   § 371 (c)(1),
   (2) Date: Apr. 28, 2023

(87) PCT Pub. No.: WO2023/016469
   PCT Pub. Date: Feb. 16, 2023

(65) Prior Publication Data
   US 2024/0008943 A1     Jan. 11, 2024

(30) Foreign Application Priority Data

Aug. 11, 2021   (CN) .......................... 202110921449.1
   Jan. 30, 2022   (CN) .......................... 202210114658.X
                        (Continued)

(51) Int. Cl.
   *A61B 34/37*        (2016.01)
   *A61B 34/30*        (2016.01)
                        (Continued)

(52) U.S. Cl.
   CPC ........ *A61B 34/37* (2016.02); *A61B 2034/301* (2016.02); *A61F 2/95* (2013.01);
                        (Continued)

(58) Field of Classification Search
   None
   See application file for complete search history.

(56)                References Cited

U.S. PATENT DOCUMENTS

2009/0138025 A1*   5/2009   Stahler ................... A61B 34/71
                                                                606/130
   2010/0069833 A1    3/2010   Wenderow et al.
                        (Continued)

FOREIGN PATENT DOCUMENTS

CN          102144943 A      8/2011
   CN          105407825 A      3/2016
                        (Continued)

*Primary Examiner* — Deborah L Malamud
(74) *Attorney, Agent, or Firm* — NKL Law; Bin Lu; Allen Xue

(57)                ABSTRACT

A surgical robot system has a terminal execution system that includes a guide wire control module, a balloon/stent control module and a guide catheter control module. The guide wire control module has a rotating assembly having a rotating wheel set, a rotary shaft concentrically connected to the rotating wheel set, a planet gear sleeved on the rotary shaft and slidable relative to the rotary shaft, and a sun gear meshing with the planet gear. A wire slot for embedding a guide wire is disposed on the sun gear. The guide wire control module also includes an advancing assembly having an advancing wheel set, a transmission screw concentrically connected to a bevel gear of the advancing wheel set, and a fixed disk for supporting the sun gear. The surgical robot system can control the rotation, advancing and retreating of a guide wire, as well as a balloon catheter or stent catheter.

9 Claims, 30 Drawing Sheets

(30)          Foreign Application Priority Data

| Jan. 30, 2022 | (CN) | .......................... | 202210114671.5 |
| Jan. 30, 2022 | (CN) | .......................... | 202210120116.3 |

(51)  Int. Cl.

| *A61F 2/95* | (2013.01) |
| *A61M 25/01* | (2006.01) |
| *A61M 25/09* | (2006.01) |
| *A61M 25/10* | (2013.01) |

(52)  U.S. Cl.
CPC ...  *A61M 25/0113* (2013.01); *A61M 25/09041*
               (2013.01); *A61M 25/10* (2013.01)

(56)              References Cited

U.S. PATENT DOCUMENTS

| 2018/0168751 A1 | 6/2018 | Yi et al. |
| 2020/0297439 A1 | 9/2020 | Cameron et al. |

FOREIGN PATENT DOCUMENTS

| CN | 206526069 U | 9/2017 |
| CN | 108158656 A | 6/2018 |
| CN | 108697474 A | 10/2018 |
| CN | 112120745 A | 12/2020 |
| CN | 113598947 A | 11/2021 |
| CN | 215024793 U | 12/2021 |
| EP | 2821094 A1 | 1/2015 |
| WO | 2019118367 A1 | 6/2019 |
| WO | 2021011533 A1 | 1/2021 |

* cited by examiner

SURGICAL ROBOT SYSTEM

TECHNICAL FIELD

The invention relates to the field of medical devices, and more specifically to a surgical robot system.

BACKGROUND

Interventional surgery is based on imaging, guided by X-ray, ultrasound or CT, using guidewires, catheters or stents, and other medical devices to diagnose and treat diseases. It is a relatively advanced minimally invasive technology. Manual insertion of a catheter or guide into a patient is a relatively routine surgical procedure. Attempts are currently being made to robotic this insertion. This kind of robotization is very complicated, because it is very difficult to grasp the catheter, and the catheter is smooth and must remain sterile during the operation. These factors increase the difficulty of robotization. Despite these difficulties, the reliability and accuracy of this robot system are still the decisive factors accepted by the medical community.

As a result, there is a lack of a surgical robotic system that is simpler to operate and more reliable in the art.

SUMMARY

Based on the market demand in this field, the present invention has developed a surgical robot system, which can remotely control the rotation, advancement and retraction of the guide wire control module, the catheter/balloon/bracket control module and the guide catheter control module through the remote microcomputer control end; form a space gap between the execution housing and the drive housing of the terminal execution system through the non-contact motor system to place aseptic cloth and other items to reduce pollution, without affecting the normal operation of the vascular intervention robot; effectively position the guide catheter control module before the operation through the rack and pinion group for the guide catheter, and does not interfere with the relative movement between the components of the module during the operation, avoiding the loss of precision due to unwanted relative displacements between the components; effectively locate the axial position and radial position of the sun gear in the guide wire control module by means of a positioner assembly, as well as controlling the dynamic and static state of the surgical robot arm, ensuring the safety of the robot and the accuracy of adjusting the guide wire; moving the driving components such as the motor, the transmission rod, etc. into the drive housing, reducing the occupation of the space in the execution housing, so that there is more guide wire operating space in the execution housing, and it is convenient to clean the execution housing. The mechanical braking in the present invention is mainly realized by the meshing between the gears and the transmission effect of the transmission rod. The invention is convenient to operate and precise in regulation.

The invention provides a surgical robot system, which comprises a remote microcomputer control end, a surgical robot arm and a terminal execution system. Wherein, the terminal execution system includes a guide wire control module configured to control advance, retreat and rotation of a guide wire, and the guide wire control module comprises: a rotating assembly configured to control the rotation of the guide wire, the rotating assembly including a rotating wheel set, a rotating shaft concentrically connected to the rotating wheel set, a planet gear sleeved on the rotating shaft and slidable relative to the rotating shaft, and a sun gear meshing with the planet gear, wherein the sun gear is provided with a wire slot, which opens from a valley between teeth of the sun gear to center of the sun gear, and is structured to insert the guide wire and ensure coaxial rotation of the guide wire; and a traveling component configured to control the advance or retreat of the guide wire, the traveling component including a traveling wheel set, a transmission screw concentrically connected with a bevel gear of the traveling wheel set, and a fixed disk for supporting the sun gear; a balloon/stent control module configured to control advance or retreat of a balloon catheter or a stent catheter, including a transmission wheel assembly comprising a friction wheel set, wherein under the friction wheel set, there are friction wheel set gears meshing with each other, and the friction wheel set clamps the balloon catheter or the stent catheter to move it advance or retreat; and a guide catheter control module configured to control advance or retreat of the guide catheter, including a Y-typed assembly, the Y-typed assembly including an upper Y-typed valve and a lower rack and pinion group, wherein a distal port of the Y-typed valve is connected to the guide catheter, and a proximal port is penetrated the guide wire, the guide wire enters the guide catheter through the Y-typed valve and reaches a surgical site along lumen of the guide catheter, and the rack and pinion group drives the Y-typed assembly forward or backward, thereby driving the guide catheter forward or backward; wherein, the rotating wheel set, the traveling wheel set, the friction wheel set and the Y-typed assembly are all driven by motors and connected with a remote microcomputer.

In another preferred embodiment, the rotation of the rotating wheel set in the guide wire control module drives the concentrically connected rotating shaft to rotate together, and the rotating shaft drives the planet gear to rotate, the planet gear drives the sun gear to rotate through meshing effect, thereby driving the rotation of the guide wire.

Rotation of a bevel gear of the traveling wheel set drives the transmission screw rod to rotate, the fixed disk is threadedly meshed with the transmission screw rod, and advances or retreats with rotation of the transmission screw rod, and an advance or retreat of the fixed disk drives the guide wire to advance or retreat.

In another preferred embodiment, gears of the friction wheel set of the transmission wheel assembly in the balloon/bracket control module rotates to drive the friction wheels above to rotate, and rotation of the friction wheels drives the forward or backward movement of the balloon catheter or stent catheter clamped by the friction wheels.

In another preferred embodiment, a gear(s) in the rack and pinion group of the Y-typed assembly in the guide catheter module drives a rack(s) meshed therewith to move, so that the Y-typed valve and the guide catheter thereto advance or retreat.

In another preferred embodiment, in longitudinal direction of the entire system, a plurality of wire slots are provided from the proximal end to the distal end, which can directly place the guide wire from top to bottom, including an outer box, a wheel set, a slidable rod and a fixed plate, so as to facilitate the placement of the guide wire before the surgery and the removal and exchange of the guide wire during the surgery, and also facilitate the cooperation of the guide wire and the balloon catheter or stent catheter.

In another preferred embodiment, at least two fixed gears are provided on the fixed disk, and the fixed gears are meshed with the sun gear for fixing the sun gear.

In another preferred embodiment, the guide wire control module includes a locking device for locking the guide wire, and the locking device is fixed to the sun gear.

In another preferred embodiment, the locking device comprises a locking control assembly, an active member and a fixed member, wherein the fixed member is fixed to the sun gear and aligned with one side of the wire slot, the active member is provided opposite to the fixed member and aligned with the other side of the wire slot, and the locking control assembly is connected to the active member for controlling the positional relationship of the active member relative to the fixed member.

In another preferred embodiment, the locking control assembly includes a key, a linkage rod, a spring and a limit block. The spring and the limit block are provided in an inner cavity of the active member. The limit block is fixed. The spring is located between the limit block and the side wall of the active member. One end of the linkage rod is connected with the key, and the other end is connected with the active member.

In another preferred embodiment, the guide wire control module includes a guide wire supporting rod, and the guide wire supporting rod is provided between the wheel set and the fixed plate.

In another preferred embodiment, an operator remotely controls the movement of the guide wire control module, the balloon/stent control module and the guide catheter control module using signal transmission through the remote microcomputer control end.

The present invention also provides a surgical robot system, which is used to control the guide wire, balloon or stent during surgery, and can control the advance, retreat and rotation of the guide wire, and can also control the advance or retreat of the balloon catheter or stent catheter and the guide catheter. The system includes a remote microcomputer control end, a surgical robot arm and a terminal execution system. Wherein, the terminal execution system includes a guide wire control module configured to control advance, retreat and rotation of a guide wire, and the guide wire control module comprises: a rotating assembly configured to control the rotation of the guide wire, the rotating assembly including rotating bevel gears, a rotating shaft concentrically connected to the rotating bevel gears, a planet gear sleeved on the rotating shaft and slidable relative to the rotating shaft, and a sun gear meshing with the planet gear, wherein the sun gear is provided with a wire slot configured to embed the guide wire therein; conveying assembly configured to control the advancement and retreat of the guide wire, the conveying assembly including a power wheel set, a transmission screw rod concentrically connected to a gear of the power wheel set, and a fixed disk for supporting the sun gear; wherein the rotating bevel gears and the power wheel set are both driven by electric motors, the rotation of the rotating bevel gears driving the rotating shaft, which is concentrically connected to it, to rotate together, the rotating shaft in turn drives the planet gear to rotate, the planet gear drives the sun gear to rotate through meshing effect; rotation of gears of the traveling wheel set drives the transmission screw rod to rotate, and the fixed disk is threadedly meshed with the transmission screw rod, and advances or retreats with rotation of the transmission screw rod.

In another preferred embodiment, the rotation shaft is a hexagonal shaft.

In another preferred embodiment, the rotation shaft is a polygonal shaft.

In another preferred embodiment, the rotating shaft is a semi-circular shaft or a convex/concave-shaped shaft.

In another preferred embodiment, the sun gear and the planet gear are both disposed in the inner cavity of the fixed disk and move along with the forward and backward movement of the fixed disk.

In another preferred embodiment, the proximal end of the transmission screw rod is connected and fixed with the bevel gear of the traveling wheel set, a proximal end of the rotating shaft is connected and fixed with the rotating wheel set, and the distal end of the transmission screw rod and the distal end of the rotating shaft are both fixed on the fixed plate of the distal end through bearings.

In another preferred embodiment, a wire slot similar to the wire slot on the sun gear is provided on the fixed plate to allow insertion of the guide wire.

In another preferred embodiment, initial positions of the rotating wheel set and the traveling wheel set are both located at a proximal end of the system.

In another preferred embodiment, the rotating wheel set and the traveling wheel set are both located on the same cross section.

In another embodiment, a length of the transmission screw rod is 100 mm to 400 mm; preferably, 150 mm to 250 mm.

In another embodiment, the length of the rotating shaft is 100 mm to 400 mm; preferably, 150 mm-250 mm.

In another embodiment, the traveling wheel set comprises at least one pair of bevel gears; preferably, the traveling wheel set comprises two pairs of bevel gear sets.

In another embodiment, the traveling wheel set consisting of two or more pairs of bevel gear sets includes a linkage belt for connecting the bevel gears, and the linkage between the bevel gears of the traveling wheel set is realized by the linkage belt.

In another embodiment, the wire slot is opened at the bottom of the valley between the teeth of the sun gear, which does not affect the meshing between the sun gear and other gears.

In another embodiment, the wire slot is opened from the bottom of the valley between the teeth of the sun gear to the centre of the circle of the sun gear.

In another preferred embodiment, the wire slot on the sun gear are tapered in the direction of the radius from the outside to the inside, so as to be configured for embedding guide wires of different diameters therein.

In another preferred embodiment, at least two fixed gears are provided on the fixed disk, and the fixed gears are meshed with the sun gear for fixing the sun gear. Fixed gears can be two or multiple.

In another preferred embodiment, the fixed disk is a hollow disk, the sun gear, the planet gear and the fixed wheel(s) are disposed in a hollow cavity of the fixed disk, and the fixed disk is further provided with a radial opening for embedded the guide wire.

In another preferred embodiment, the sun gear and the fixed disk are concentrically aligned.

In another preferred embodiment, the system comprises a locking device for locking the guide wire, and the locking device is fixed to the sun gear.

In another preferred embodiment, the locking device comprises a locking control assembly, an active member and a fixed member, the fixed member is fixed to the sun gear and aligned with one side of the wire slot, the active member is provided opposite to the fixed member and aligned with the other side of the wire slot, and the locking control assembly is connected to the active member for controlling the positional relationship of the active member relative to the fixed member.

In another preferred embodiment, the locking control assembly controls the active member away from the fixed member, i.e. the wire slot forms a passage that can be embedded into the guide wire.

In another preferred embodiment, the locking control assembly controls the active member against the fixed member to clamp the guide wire embedded into the wire slot.

In another preferred embodiment, the locking device may be a motorized clamp structure, which is electrically driven.

In another preferred embodiment, the locking device may be a pneumatic clamp arrangement, which is pneumatically driven.

In another preferred embodiment, the locking control assembly includes a key, a linkage rod, a spring and a limit block. The spring and the limit block are provided in the inner cavity of the active member. The limit block is fixed. The spring is located between the limit block and the side wall of the active member. One end of the linkage rod is connected with the key, and the other end is connected with the active member 21.

When the locking device is in the loosened state, by pressing the key, the linkage rod is driven to move outward, thereby driving the active member to move radially outward, and the active member is moved away from the fixed member, and this time, the spring is in a compressed state. When the locking device is in the locked state, the pressing control of the key is released, and under the action of the elastic force of the spring, the active member moves radially inward and abuts against the fixed member, and the key returns to the initial position.

In another preferred embodiment, the contact surface between the active member and the fixed member are toothed clamping surfaces to provide a greater clamping force to the guide wire.

In another preferred embodiment, the system comprises a guide wire supporting rod disposed between the sun gear and the fixed plate.

In another preferred embodiment, the guide wire supporting rod is slidable along the axial direction of the guide wire.

In another preferred embodiment, the guide wire supporting rod includes a supporting frame and pulleys on both sides. The supporting frame is provided with a wire slot corresponding to the wire slots on the sun gear and the fixed plate. In the use state, the guide wire is embedded in the wire slot, and the pulleys on both sides can move in the corresponding sliding grooves on the two side walls, respectively.

In another preferred embodiment, the sliding grooves start at the two side wall surfaces corresponding to the middle section of the sun gear and the fixed plate, and ends at the two side wall surfaces corresponding to the fixed plate.

In another preferred embodiment, the sliding grooves start at the two side wall surfaces corresponding to the sun gear and ends at the two side wall surfaces corresponding to the fixed plate. A stop member(s) is provided on the sliding grooves corresponding to the middle section of the sun gear and the fixed plate, and the stop member is used to stop the guide wire supporting rod from continuing to slide in the direction of the sun gear.

In another preferred embodiment, the guide wire supporting rod is provided with a first magnet, and correspondingly, the fixed plate is provided with a second magnet, and the first magnet and the second magnet attract each other.

In the operation of transporting the guide wire, the guide wire supporting rod is initially located in the middle section between the sun gear and the fixed plate and the guide wire is placed in the wire slot. As the fixed disk moves distally along the transmission screw rod, the second magnet and the first magnet generate attraction, and the guide wire supporting rod continues to move distally together with the fixed disk. In the operation of retracting the guide wire, the guide wire supporting rod retracts to the proximal end together with the fixed disk, when retracted to the middle section between the sun gear and the fixed plate, under the blocking effect of the stop member or the walls of the sliding grooves, the guide wire supporting rod is no longer retracted and is fixed, while the fixed plate can continue to be retracted.

In another preferred embodiment, all of the wire slots form a passage from the proximal end to the center of the Y-typed valve.

In another preferred embodiment, the system comprises at least one pair of guide wire drive wheels for distally supporting and delivering the guide wire.

In another preferred embodiment, the guide wire transmission wheel is disposed on the distal end side of the fixed plate and is 5 mm to 15 mm (center distance) away from the fixed plate.

In another preferred embodiment, the joint of the guide wire transmission wheel corresponds to the wire slot on the fixed plate.

In another preferred embodiment, the guide wire is placed between at least one pair of the guide wire transmission wheels, and the guide wire is transported by friction between at least one pair of the guide wire transmission wheels.

In another preferred embodiment, at least one pair of the guide wire transmission wheels is provided with at least one pair of locking switches for controlling a distance between the pair of the guide wire transmission wheels, thereby controlling a locking condition of at least one pair of the guide wire transmission wheels.

In another preferred embodiment, the system comprises at least one set of transmission wheel sets for supporting and delivering the balloon or stent catheter.

In another preferred embodiment, the balloon catheter or stent catheter is placed between at least one set of transmission wheels, the balloon catheter or stent catheter being delivered by friction between the at least one set of transmission wheels.

In a further preferred embodiment, at least one set of transmission wheels is provided with at least one pair of locking switches for controlling the distance between one set of transmission wheels, thereby controlling a locking condition of at least one set of transmission wheels.

In another preferred embodiment, the system comprises a Y-typed assembly for a Y-typed rapid combination of the guide wire and guide catheter, the Y-typed assembly is movable, and the forward and backward movement of the guide catheter is controlled by movement of the Y-typed assembly.

It should be noted that the movement of the Y-typed assembly can transport or withdraw the guide catheter.

In another embodiment, the Y-typed assembly is disposed at the distal end of the system, 10-200 mm from the fixed plate (center distance); preferably, 80-120 mm.

In another preferred embodiment, the Y-typed assembly is moved back and forth by engagement of gear(s) and a rack(s).

In another embodiment, the Y-typed assembly is fixedly connected to the rack, the gear is connected to the motor, and the gear and the rack are engaged with each other.

When in use, the motor drives the gear to rotate, and under the action of meshing, the rack moves forward or backward, thereby driving the Y-typed assembly forward or backward.

In another embodiment, the number of the gears is two, which are respectively a driving gear and a driven gear. The driving gear and the driven gear are meshed with each other, and two racks are correspondingly provided. The driving gear and the driven gear are respectively meshed with the two racks.

In another embodiment, the number of the gears is one, the number of the racks is one, and the gear is meshed with the rack.

In another embodiment, the Y-typed assembly is openable and closable, and in the open state, rapid exchange of the guide wire and the balloon or stent catheter may be performed.

In another embodiment, the Y-typed assembly is foldable, the Y-typed assembly having a foldable angle of 0-60 degrees.

In another embodiment, the Y-typed assembly may control the rotation of the guide catheter.

In another preferred embodiment, the operator remotely controls the movement of the guide wire control module, the balloon/stent control module and the guide catheter module using signal transmission through the remote microcomputer control end.

It should be noted that the front end of the Y-typed valve (Y-typed assembly) is connected to the guide catheter, and the forward and backward movement of the guide catheter is controlled by controlling the forward and backward movement of the Y-typed valve. The transmission wheel group clamps the balloon catheter or the stent catheter forward or backward. The rotating wheel set and the traveling wheel set control the rotation, forward or backward of the wheel set that clamps the guide wire. The rotation, forward or backward of all components can be done by the operator controlling the terminal controller outside the operating room.

In another embodiment, the system communicates with the terminal controller through wired, wireless (WiFi, Bluetooth, etc.) or the Internet.

In another embodiment, the operation terminal is a computer.

In another embodiment, the operation terminal includes a tablet computer and a joystick, and the operator adjusts the forward or backward distance of the guide wire and the rotation angle of the guide wire, adjusts the forward or backward distance of the guide catheter and the rotation angle of the guide catheter, and adjusts the forward or backward distance of the balloon catheter or the stent catheter by adjusting the parameters displayed on the tablet computer, and then operate the joystick to control the forward, backward or rotating of the guide wire, the forward or backward of the balloon catheter or stent catheter, and the forward, backward or rotating of the guide catheter.

In another embodiment, the system is placed in an outer box, and the outer box has a length of 400-800 mm, a width of 150-300 mm, and a height of 50-200 mm.

In another embodiment, the diameter of the sun gear is 20-80 mm.

In another embodiment, the planet gear and the at least two fixed gears have the same specifications, and their diameters are both 15-30 mm.

In another embodiment, the specification of the planet gear differ from the specifications of the at least two fixed gears.

In another embodiment, the diameter of the gears of the traveling wheel set is 15-30 mm.

In another embodiment, the diameter of the guide wire transmission wheel is 5-20 mm.

In another embodiment, the sleeve has a diameter of 80-200 mm and a length of 250-600 mm.

In another embodiment, the Y-typed assembly has a length of 50-120 mm, a width of 30-60 mm, and a height of 10-40 mm.

In another embodiment, the diameters of both the driving gear and the driven gear of the Y-typed assembly are 5-20 mm.

In another embodiment, the number of integral component comprising the rotating assembly, the delivery assembly and its accessories, i.e. the guide wire control module, can be stacked to deliver a plurality of different guide wires to enable the exchange of guide wires during surgery. In another embodiment, there can be more than two wire slots on the fixed plate, and when two to three guide wires are used in the operation, the wire slots are embedded in each of the guide wires.

In another embodiment, the system is made of PC, nylon and other plastic materials or 304, 316 stainless steel and other metal materials, which are non-toxic to human body, can be disinfected and sterilized, and is low in price, suitable for one-time use.

In another embodiment, the system comprises a non-contact motor system, and the non-contact motor system is provided on the terminal execution system for providing a drive force for forward, backward and rotational movement of the interventional device; the non-contact motor system includes a motor, a first magnetic induction coupling coupled to the motor and driven by the motor, a second magnetic induction coupling corresponding to the first magnetic induction coupling, and a transmission structure coupled to the second magnetic induction coupling; wherein the first magnetic induction coupling and the second magnetic induction coupling are coaxially opposed; and a distance between the first magnetic induction coupling and the second magnetic induction coupling is 0-20 mm; preferably, 2-20 mm.

In another preferred embodiment, the number of the non-contact motor systems is 2-10.

In another preferred embodiment, the terminal execution system includes an execution housing loaded with mechanical components for driving forward, backward, and rotational movement of the interventional device, and a drive housing loaded with electrically powered components for powering the mechanical components.

In another preferred embodiment, the motor is fixed in the drive housing, and the second magnetic induction coupling is fixed on a bottom wall of the execution housing.

In another preferred embodiment, under the support of the pair of first and second magnetic induction couplings, a space layer having a thickness of 2-20 mm is formed between the execution housing and the drive housing.

In another preferred embodiment, the first magnetic induction coupling is fixed to the motor shaft of the motor by means of a top wire or pin.

In another preferred embodiment, the transmission structure is a gear set structure or a worm structure.

In another preferred embodiment, the terminal execution system includes a guide wire control module in the interventional device, and the guide wire control module includes a rotating assembly that controls the rotation of the guide wire through a rotating wheel set and a traveling assembly that controls the guide wire to advance or retreat through a traveling wheel set; wherein the rotating wheel set and the traveling wheel set are both driven by the non-contact motor system(s).

In another preferred embodiment, the terminal execution system comprises a balloon/stent control module in the interventional device that controls the advance or retreat of the balloon catheter or stent catheter through a friction wheel set, and a guide catheter control module in the interventional device that controls the advance or retreat of the guide catheter through a rack and pinion group; wherein the friction wheel set and the rack and pinion group are both driven by the non-contact motor system(s).

In another preferred embodiment, the rack and pinion group includes a rack frame, and the Y-typed valve is fixed on the rack frame; a gear, and the gear is meshed and connected with a straight rack on the rack frame; a moving magnetic member installed on the rack frame; and a fixed magnetic member acting on the moving magnetic member; wherein the fixed magnetic member is fixed on the housing of the terminal execution system.

In another preferred embodiment, the rack frame includes a first toothed edge, a second straight edge, and a third connecting edge.

In another preferred embodiment, the first toothed edge is provided with a straight rack meshing with the gear, and the second straight edge and the first toothed edge are provided parallel and opposite to each other.

In another preferred embodiment, the third connecting edge connects the first toothed edge and the second straight edge to form a semi-enclosed structure, and the gear is placed in the semi-enclosed structure.

In another preferred embodiment, one end of the single gear meshes with the straight rack of the first toothed edge, and the other end of the single gear abuts against the second straight edge.

In another preferred embodiment, the moving magnetic member is fixed on the third connecting edge.

In another preferred embodiment, the moving magnetic member is fixed on the first edge or the second edge.

In another preferred embodiment, the rack frame interacts with the fixed magnetic member fixed on the housing of the terminal execution system through the moving magnetic member, so as to prevent the rack frame from sliding randomly.

In another preferred embodiment, during the operation, the driving device drives the gear to rotate, due to the meshing relationship between the gear and the rack frame, the rack frame overcomes the force generated by the fixed magnetic member and moves forward, thereby driving the Y-typed valve to move forward.

In another preferred embodiment, the system comprises a positioner assembly, the positioner assembly comprises a guide wire control module positioner, and the guide wire control module positioner is configured for the positioning of the guide wire control module of the terminal execution system; the guide wire control module is configured to control advance, retreat and rotation of a guide wire, comprising: a rotating assembly configured to control the rotation of the guide wire, including a rotating wheel set, a rotating shaft concentrically connected to the rotating wheel set, a planet gear sleeved on the rotating shaft and slidable relative to the rotating shaft, and a sun gear meshing with the planet gear, wherein the sun gear is provided with a wire slot, which opens from a valley between teeth of the sun gear to center of the sun gear, and is configured to insert the guide wire and ensure the coaxial rotation of the guide wire; and a traveling component configured to control the advance or retreat of the guide wire, including a traveling wheel set, a transmission screw concentrically connected with a bevel gear of the traveling wheel set, and a fixed disk for supporting the sun gear; the guide wire control module positioner includes a first sensing point provided at the bottom of the fixed disk, a first inductor for sensing the first sensing point; a second sensing point provided at an end of the sun gear opposite to the wire slot, a second inductor for sensing the second sensing point; the first inductor and the second inductor are provided at the bottom of the terminal execution system; wherein the first inductor determines the position of the fixed disk by sensing the first sensing point, and in the case of determining the position of the fixed disk, the second sensor determines the angular position of the sun gear by sensing the second sensing point.

In another preferred embodiment, the first inductor and the second inductor are both laser sensors.

In another preferred embodiment, the first inductor and the second inductor are both infrared sensors.

In another preferred embodiment, the first inductor and the second inductor are both electromagnetic inductors.

In another preferred embodiment, the inductors may have two or more pairs.

During operation, move the fixed disk, and when the first inductor senses the first sensing point at the bottom of the fixed disk (the first sensing point is directly above the first inductor), stop moving the fixed disk. At this time, the fixed disk is in the setting position, that is, the guide wire control module is axially positioned. Then, the sun gear is rotated, and the locking device protruding fixed to the sun gear rotates accordingly. When the second inductor senses the second sensing point on the end of the locking device opposite to the wire slot (the second sensing point is directly above the second sensor), the rotating of the sun gear is stopped, that is, the guide wire control module is radially positioned.

In another preferred embodiment, both the first inductor and the second inductor are disposed on the drive housing.

In another preferred embodiment, inductor opening(s) is provided on the execution housing at a position corresponding to the first inductor and the second inductor on the drive housing, and the first inductor and the second inductor sense the first sensing point and the second sensing point respectively through the inductor opening(s).

In another preferred embodiment, the bottom wall of the execution housing is transparent.

In another preferred embodiment, the air layer between the execution housing and the drive housing is provided with a isolation cloth for blocking contamination of components in the drive housing during surgery.

In another preferred embodiment, the isolation cloth is transparent at the part corresponding to the two inductors.

In another preferred embodiment, the positioner assembly further comprises a surgical robot arm positioner disposed on the drive housing of the terminal execution system for sensing whether the execution housing is located on the drive housing.

In another preferred embodiment, the surgical robot arm is fixed when the surgical robot arm positioner senses that the execution housing is located above the drive housing, and the surgical robot arm is free to move when the surgical robot arm positioner senses that the execution housing is removed from above the drive housing.

In another preferred embodiment, the surgical robot arm positioner is an infrared sensor.

In another preferred embodiment, the surgical robot arm positioner is a laser sensor.

In another preferred embodiment, the surgical robot arm positioner is an electromagnetic inductor.

The robot is used for interventional, orthopaedic, surgical and gynaecological surgery, comprising a remote microcomputer control end, a surgical robot arm and a terminal execution system, wherein the terminal execution system is fixed on the end of the surgical robot arm and moves with the surgical robot arm, and the remote microcomputer control end controls the movement of the surgical robot arm and the movement inside the terminal execution system.

In another preferred embodiment, in the guide wire control module (i.e., the guide wire movement/rotation module), one end of the guide wire is clamped to the sun gear and the other end rests on the housing barrel of the guide wire control module. At this time, a guide wire supporting sliding rod is placed between the sun gear and the housing cylinder, the guide wire supporting sliding rod has a semicircular structure with two L-shaped brackets projecting from the bottom side of the semicircular bottom edge, and the two L-shaped brackets can be embedded in the sliding rail grooves on both sides of the housing cylinder, so that the guide wire supporting sliding rod can move back and forth in the sliding rail grooves. The guide wire supporting sliding rod is provided with an embedded groove from the top to near the center of the circle, with a width of 0.1-5 mm. The height of the bottom of the embedded groove is on the same horizontal line as the center of the circle of the sun gear and the height of the guide wire resting point on the housing barrel of the guide wire control module. One round through hole is respectively opened on both sides of the semicircular structure of the guide wire supporting sliding rod. The diameter of the round through hole is 0.1-3 mm. Two flexible pipes are respectively inserted into the round through holes. After passing through the round through holes, the flexible pipes abut at the guide wire embedded groove.

In another preferred embodiment, the guide wire supporting sliding rod is provided with a first magnet, and correspondingly, the fixed plate is provided with a second magnet, and the first magnet and the second magnet attract each other.

In the operation of conveying the guide wire, the guide wire supporting sliding rod is located in the middle section between the sun gear and the housing barrel and the guide wire is placed in the embedded groove. As the fixed disk moves along the transmission screw rod to the proximal end, the second magnet and the first magnet generate an attractive effect, and the guide wire supporting sliding rod continues to move to the proximal end together with the fixed disk. In the operation of retracting the guide wire, the guide wire supporting sliding rod retracts to the distal end together with the fixed disk. When retracts to the middle position between the sun gear 15 and the housing barrel, the guide wire supporting sliding rod is no longer retracted and fixed under the blocking action of the stop member or the walls of the slide rail grooves, while the fixed disk can continue to be retracted.

In another preferred embodiment, the number of guide wire supporting sliding rods may be two or more.

In another preferred embodiment, the non-contact motor system is provided on the terminal execution system for providing drive for the transport, retraction and rotation of the guide wire; the non-contact motor system includes a motor, a first magnetic induction coupling coupled to the motor and driven by the motor, a second magnetic induction coupling provided opposite to the first magnetic induction coupling, and a transmission gear set coupled to the second magnetic induction coupling; wherein the first magnetic induction coupling and the second magnetic induction coupling are coaxially opposed; and a clearance (distance) between the first magnetic induction coupling and the second magnetic induction coupling is 2-20 mm.

In another preferred embodiment, the motor is fixed in the drive housing, and the second magnetic induction coupling is fixed on a bottom wall of the execution housing.

In another preferred embodiment, the sterile cloth is a blood-separated sterile cloth, and the positions of the sterile cloth corresponding to the inductors are transparent.

In another preferred embodiment, the transmission gear set is a bevel gear set or a flat gear set.

In another preferred embodiment, the rotating wheel set and the traveling wheel set are both driven by the non-contact motor system(s).

In another preferred embodiment, the guide wire center holder is provided on the sun gear, which has a configuration similar to the above-mentioned the embedded groove and the pair of round through hole of the guide wire supporting sliding rod. The embedded groove is provided corresponding to the wire slot for fixing the guide wire passing through the wire slot.

In another preferred embodiment, the guide wire center holder is a cylindrical structure, and is fixedly connected concentrically to the sun gear. The embedded groove is wire slotted to the center of the circle as in the case of the sun gear and corresponds to the wire slot. Round through holes are provided on both sides of the embedded groove for inserting flexible materials respectively.

In another preferred embodiment, insert the guide wire into the sun gear and the limit groove, and press the guide wire with flexible materials.

In another preferred embodiment, a guide wire locker is provided on the sun gear for locking and fixing the guide wire.

In another preferred embodiment, the guide wire locker may be fixed to the side of the sun gear.

In another preferred embodiment, the guide wire locker may be fixed or removable.

In another preferred embodiment, the guide wire locker is divided into upper and lower parts, the bottom surface of the upper part and the top surface of the lower part are both provided with semicircular grooves. In a state where the upper part and the lower part are cover closed, the two semicircular grooves are combined to form a guide wire hole, at the tail end of which a guide wire locking knob is also provided.

In another preferred embodiment, in the state where the upper part and the lower part are cover closed, the bottom surface of the upper part and the top surface of the lower part of the wire guide locker press the guide wire into place.

In another preferred embodiment, the upper part and the lower part are cover closed by magnet attraction.

It should be noted that the upper part and the lower part can also be cover closed in other ways, including but not limited to snap-fit, nesting, bonding, friction fixing, etc.

When operating the guide wire locker, remove the upper cover of the guide wire locker, insert the guide wire into the guide wire locking knob, put the guide wire into the guide wire hole, cover the upper and lower parts, tighten the guide wire locking knob, and fix the guide wire locker on the sun gear, so that the guide wire can rotate with the rotation of the sun gear and move with the movement of the sun gear.

In another preferred embodiment, the guide wire locker comprises a stud and a nut, wherein the guide wire is sandwiched between the lower edge of the stud and the upper edge of the nut, the stud and the nut are tightened, and the guide wire is clamped, wherein one of the stud and the nut is fixed to the sun gear.

In another preferred embodiment, the guide wire locker includes a clamp, wherein the clamp is mounted on the sun gear. Loosen the clamp to put in the guide wire and clamp the clamp to clamp the guide wire.

In another preferred embodiment, the guide wire includes, but is not limited to, other surgical devices such as guide wires.

The present invention also provides a surgical robot system, which comprises a remote microcomputer control end, a surgical robot arm and a terminal execution system; wherein, the terminal execution system includes a guide wire control module configured to control advance, retreat and rotation of a guide wire, and the guide wire control module comprises: rotating assembly configured to control rotation of the guide wire, the rotating assembly includes one or more planet gears, a first non-contact motor system that drives the planet gears to rotate, and a sun gear meshed with the planet gears, wherein the sun gear is provided with a wire slot, and the wire slot is configured to be embedded in the guide wire; a conveying assembly configured to control the advancement and retreat of the guide wire, the conveying assembly includes a transmission screw rod, a fixed disk for supporting the sun gear and the planet gears and a second non-contact motor system for connecting the transmission screw rod and the fixed disk; wherein the transmission screw rod is coaxially provided with the motor shaft of the motor of the second non-contact motor system, and the fixed disk moves forward and backward with the rotation of the motor of the second non-contact motor system.

In another preferred embodiment, the first non-contact motor system is attached to the second non-contact motor system.

In another preferred embodiment, the terminal execution system includes a drive housing and an execution housing, wherein the planet gear, the sun gear and the fixed disk are arranged in the execution housing, the transmission screw is arranged in the drive housing, and the drive housing and the execution housing are integrally connected through the first non-contact motor system and the second non-contact motor system, wherein, the motor of the first non-contact motor system is attached to the drive screw through an intermediate connector, and advances and retreats with the fixed disk.

In another preferred embodiment, the second magnetic induction coupling is directly connected to the fixed disk, the transmission screw rod is installed in the drive housing, the transmission screw rod is directly connected to the motor shaft of the motor that drives the transmission screw rod to rotate, the motor drives the transmission screw rod to rotate, and the intermediate connector is sleeved on the transmission screw rod and is threadedly connected with the transmission screw rod. With the rotation of the transmission screw rod, the intermediate connector can move forth and back, the first magnetic induction coupling is fixedly connected with the intermediate connector, the second magnetic induction coupling is also oriented to the side in conjunction with the first magnetic induction coupling, which is coupled to the intermediate connector located on the side, under magnetic force, so that the wheel set moves forward and backward while the motor is rotating. This structure can move the transmission screw rod from the inside of the execution housing to the inside of the drive housing. The configuration can simplify the structure in the execution housing and reduce the use of gears.

In another preferred embodiment, the first magnetic induction coupling and the second magnetic induction coupling may be connected in a contact type, and wire slots are cut in the execution housing and the drive housing along the coupling trajectory to allow for coupling movement.

In another preferred embodiment, the couplings can be a non-magnetic mechanical connection, and wire slots are cut in the execution housing and the drive housing along the coupling trajectory to allow for coupling movement.

In another preferred embodiment, the transmission screw rod, the motor that drives the transmission screw rod to rotate, the intermediate connector sleeved on the transmission screw rod, and the first magnetic induction coupling connected with the intermediate connector form a whole structure, which is located on the side of the terminal execution system or in the drive housing.

In another preferred embodiment, similarly to the motor that drives the transmission screw rod to rotate, the motor that drives the planet gear to rotate is moved to the side of the terminal execution system or in the drive housing.

In another preferred embodiment, the transmission screw rod, the motor that drives the transmission screw rod to rotate, and the motor that drives the planet gear to rotate are all moved into the drive housing.

In another preferred embodiment, the motor that drives the planet gear to rotate (e.g., via trays, carriers, etc.) is attached to the intermediate connector and travels in synchronization with the wheel set as the transmission screw rod rotates.

In another preferred embodiment, the planet gears are all fixed in the fixed disk at substantially uniform intervals through smooth axes, wherein the planet gear is rotatable relative to its smooth axis, and one of the planet gears is engaged with the second magnetic induction coupling through a worm, a transmission gear (group), etc.

In another preferred embodiment, when the motor drives the transmission screw rod to rotate, the wheel set is driven by an intermediate connector connecting with the magnetic induction coupling set, and at the same time, with the rotation of the transmission screw rod, the motor that drives the planet gear to rotate travels synchronously with the wheel set, the motor that drives the planet gear to rotate drives the planet gear in the fixed disk to rotate through another magnetic induction coupling set, in turn, the sun gear engaged with the planet gear is caused to rotate.

In another preferred embodiment, a support guide rail is provided below the motor that drives the planet gears to rotate, for supporting and guiding the motor that drives the planet gears to rotate.

In another preferred embodiment, the support guide rail comprises a guide rail disposed on the drive housing and a roller attached below the motor that drives the rotation of the planet gear, wherein the roller can slide in the guide rail so as to play a supporting and guiding role.

In another preferred embodiment, the support guide rail is a smooth-surfaced guide strip disposed on the drive housing, the upper surface of the guide strip is in sliding contact with the lower surface of the motor that drives the rotation of the planet gears (or by means of magnetic suspension support guide, etc.) to provide support and guidance.

In another preferred embodiment, the Y-typed assembly further includes a guide catheter support member for supporting the guide catheter extending out of the Y-typed valve to avoid sagging and collapsing caused by the long-distance extension from the Y-typed valve;

In another preferred embodiment, the guide catheter support member comprises a sliding sleeve, a sliding sleeve handle and a sliding sleeve track.

In another preferred embodiment, a sliding sleeve track is provided in the Y-typed valve for accommodating the sliding sleeve, and the sliding sleeve can slide in the sliding sleeve track to extend out of the Y-typed valve or withdraw into the Y-typed valve.

In another preferred embodiment, the sliding sleeve handle is provided at the distal end of the sliding sleeve (one end away from the operator), and the operator can control the travel of the guide catheter by dragging the sliding sleeve handle.

In another preferred embodiment, the sliding sleeve handle is a projection located at the distal end of the sliding sleeve.

In another preferred embodiment, the upper part of the sliding sleeve is provided with an axial slit through which the guide catheter can enter and be contained within the sliding sleeve.

In another preferred embodiment, when the guide catheter extends out of the Y-typed valve for a long distance, the sliding sleeve is pulled out of the sliding sleeve track by pulling the sliding sleeve handle to support the extended guide catheter.

It should be noted that the surgical robot system of the present application can be applied to interventional surgery, orthopedic surgery, surgery and gynecological surgery. Surgical instruments used include, but are not limited to, guide wires, guide catheters, balloon catheters, and stents.

The main advantages of the present invention comprise:

(a) The robotic operation allows the operator to manipulate the instruments remotely from outside the operating room, avoiding radiation damage to the operator;

(b) The robotic operation improves the accuracy of operation compared to manual operation;

(c) The robotic operation is less likely to result in fatigue or other errors due to long periods of concentration or other reasons, as with manual operation, and is more stable;

(d) Remote robotic operation enables the separation of doctor and patient and reduces the risk of infection for both operator and patient;

(e) The couplings are connected by magnetic induction, without precise aperture fit, and easy alignment;

(f) The sterile cloth effectively isolates the contamination of non-cleanable parts, and the transparent parts of the sterile cloth effectively ensure the transmission of light for more accurate sensing of the induction;

(g) Precise positioning of the components in the module before surgery to improve the motion accuracy of each component during surgery;

(h) The terminal execution system is layered to make the functional modules clearer and easier to install;

(i) Effectively locate the axial position and radial position of the sun gear in the guide wire control module, and control the dynamic and static state of the surgical robot arm, which improves the accuracy of the control of the guide wire, so that the guide wire can reach the lesion more accurately and ensures the success rate of surgery;

(j) Relocation of drive components such as motors, transmission rods, etc. into the drive housing, reducing the occupation of space in the execution housing and allowing more space for assembly and manipulation of surgical equipment in the execution housing;

(k) Support the guide catheter extending from the Y-typed valve through the guide catheter support member to avoid sagging and collapsing caused by the long-distance extension from the Y-typed valve;

(l) The safety of the surgical robot is improved.

It should be understood that within the scope of the present invention, the above-mentioned technical features of the present invention and the technical features specifically described in the following (such as Examples) can be combined with each other to form a new or preferred technical solution. For the sake of space, they will not be repeated here.

BRIEF DESCRIPTION OF THE DRAWINGS

In order to illustrate the technical solutions in the embodiments of the present invention or in the prior art more clearly, the drawings required for the description of the embodiments or the prior art will be briefly described below. Obviously, the drawings in the following description are only some embodiments of the present invention, and those of ordinary skill in the art may obtain other drawings according to these drawings without creative efforts.

In each figure, references are as follows.

Figure 1A:
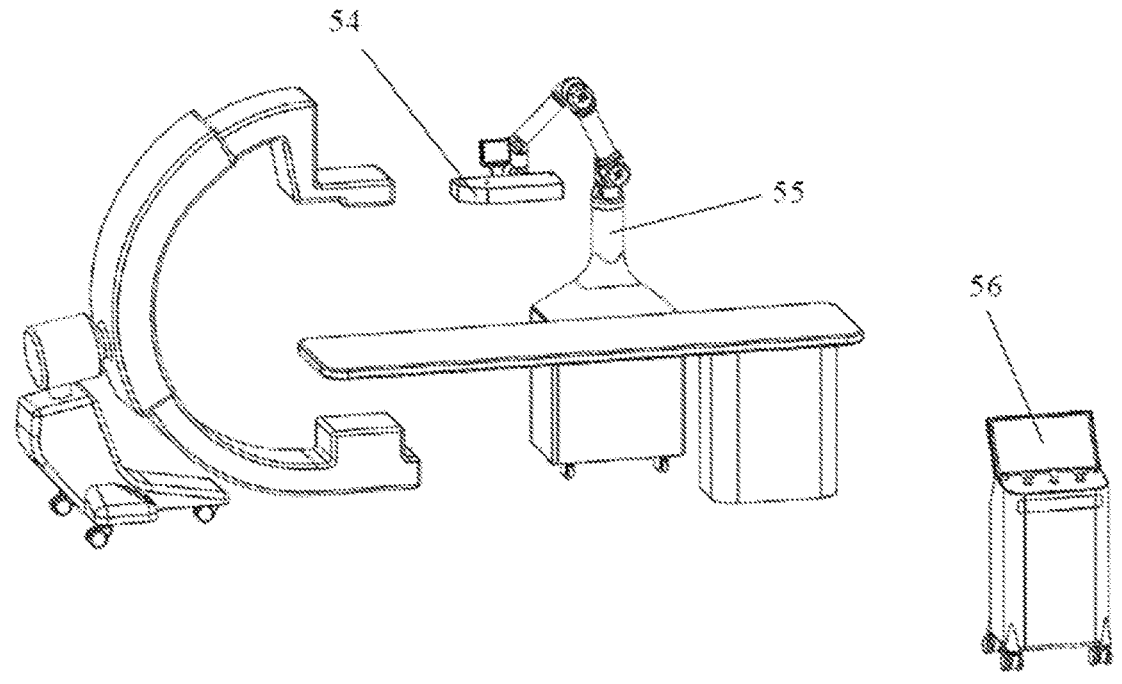
FIG. 1a is a schematic diagram of the layout of an operating room with a surgical robotic system according to an example of the present invention.
Figure 1B:
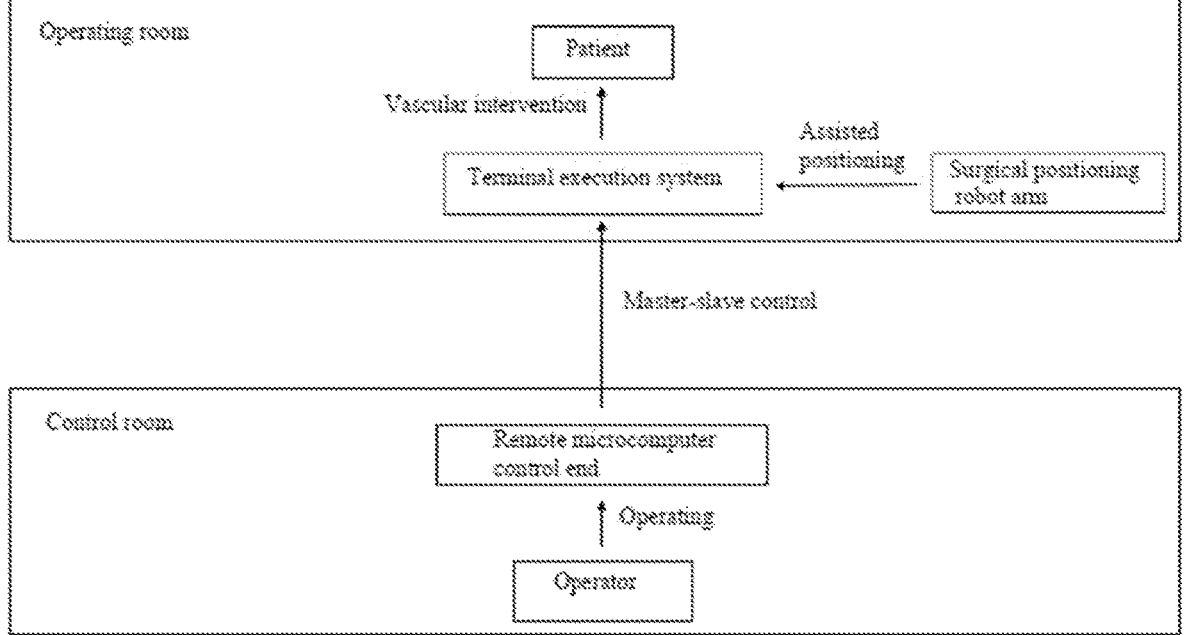
FIG. 1b is a flow diagram of the operation with the surgical robot system according to an example of the present invention.
Figure 2:
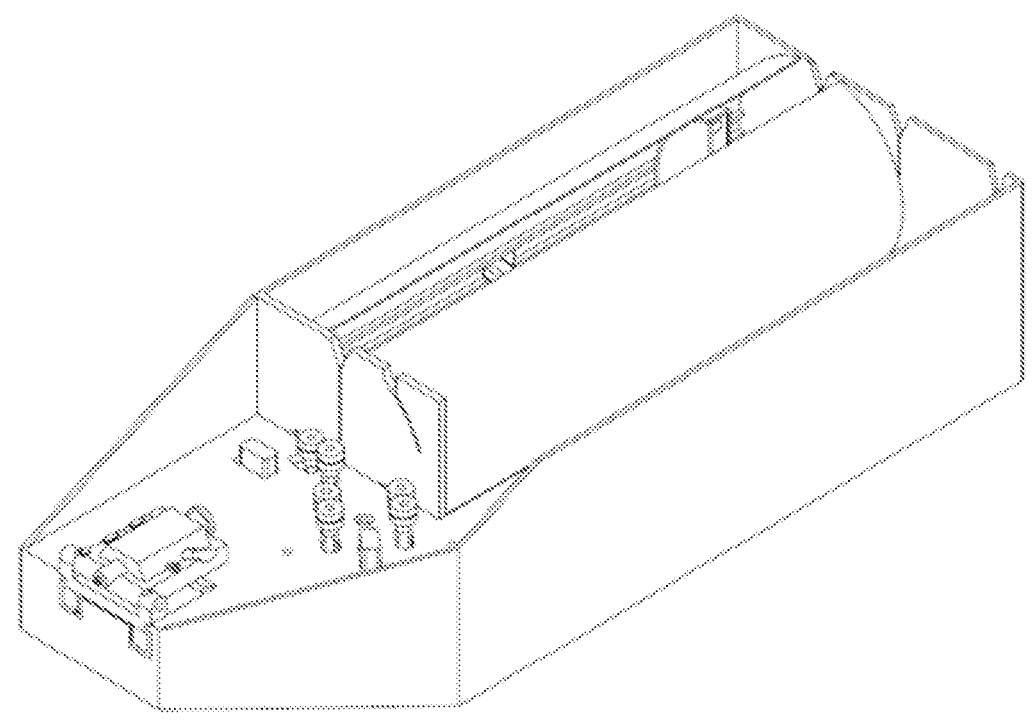
FIG. 2 is a perspective view of the execution housing of the surgical robot system according to an example of the present invention.
Figure 3:
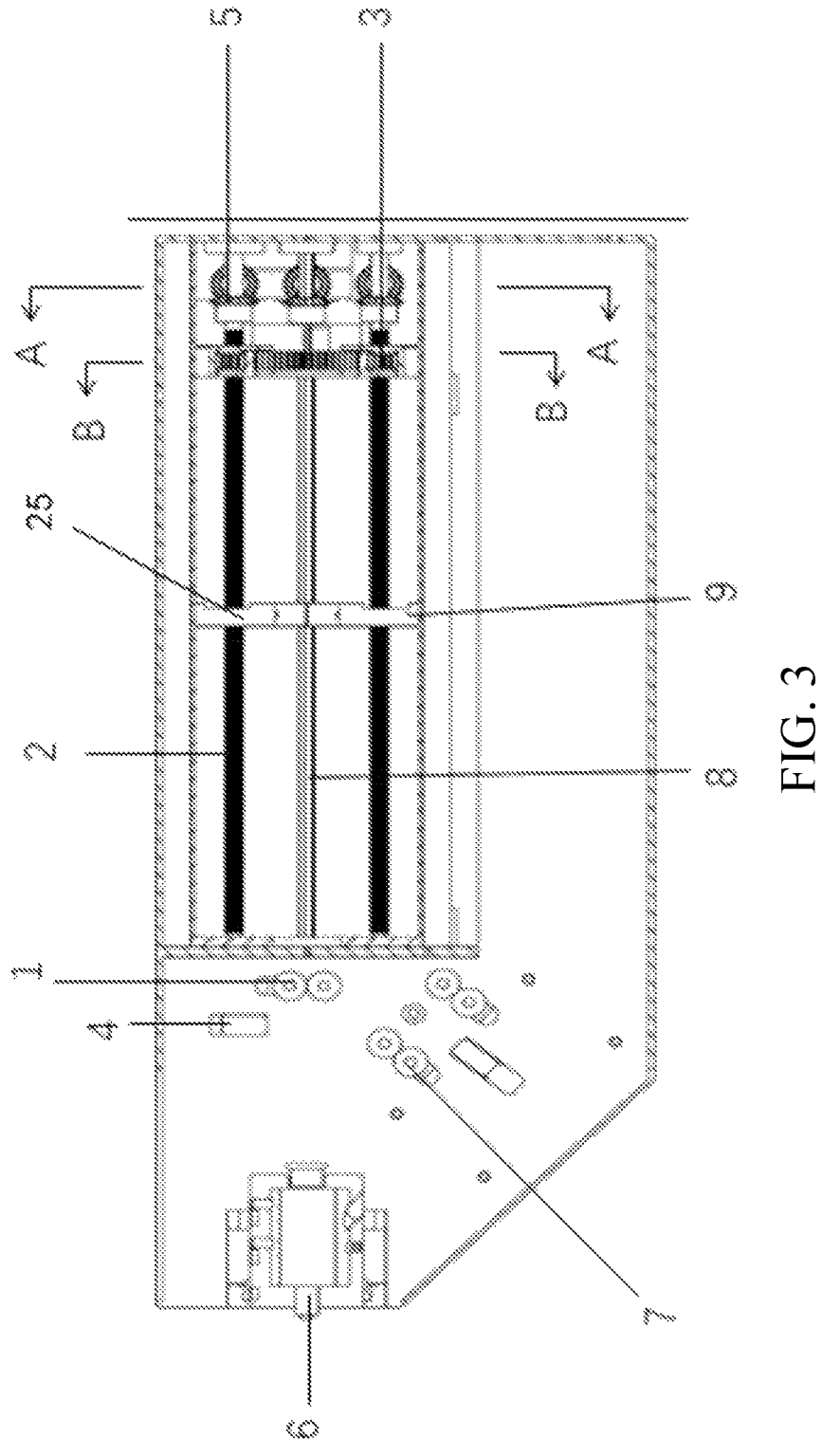
FIG. 3 is a top view of the execution housing in FIG. 2.
Figure 4:
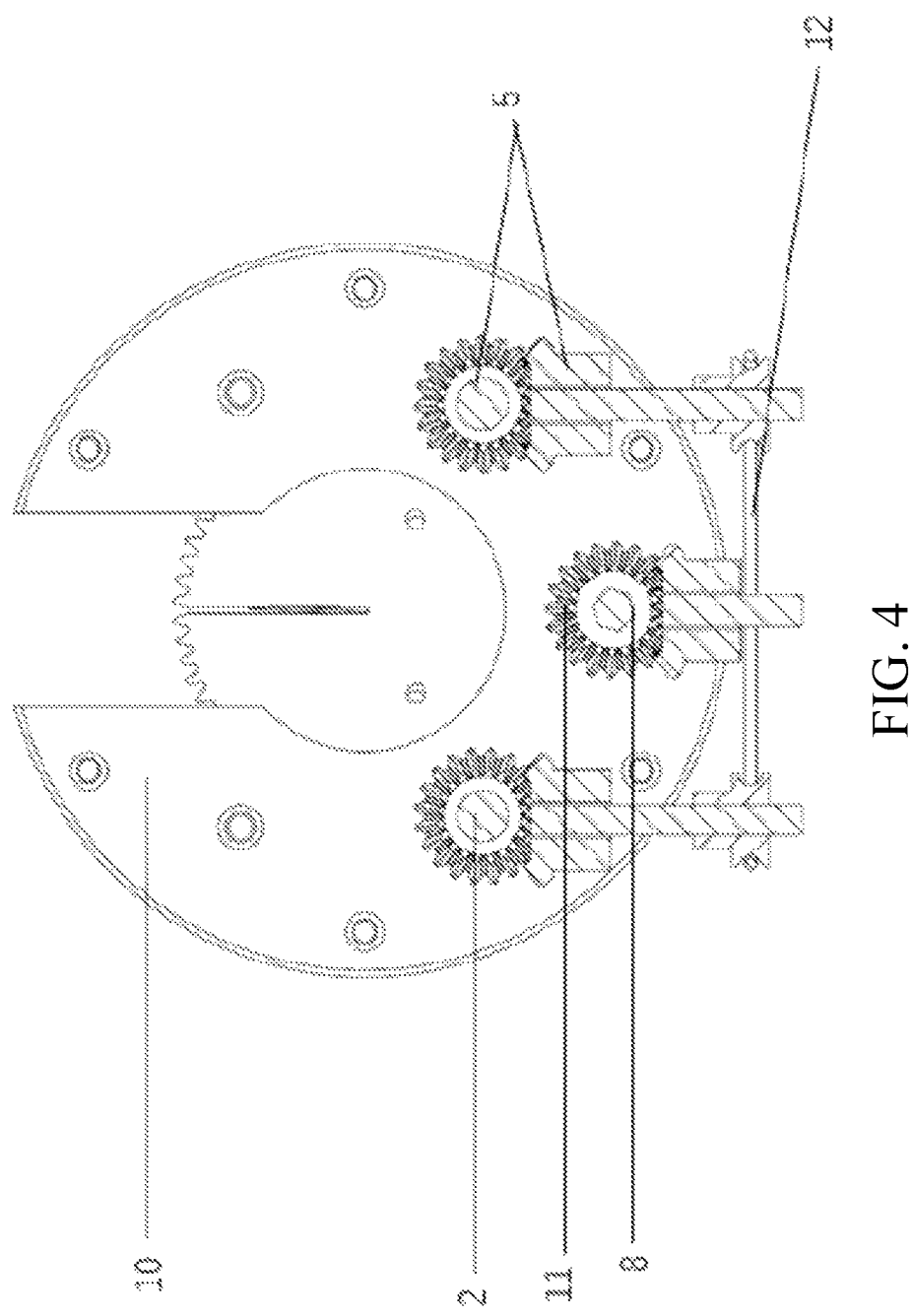
FIG. 4 is a cross-sectional view taken along the A-A section of FIG. 3.
Figure 5:
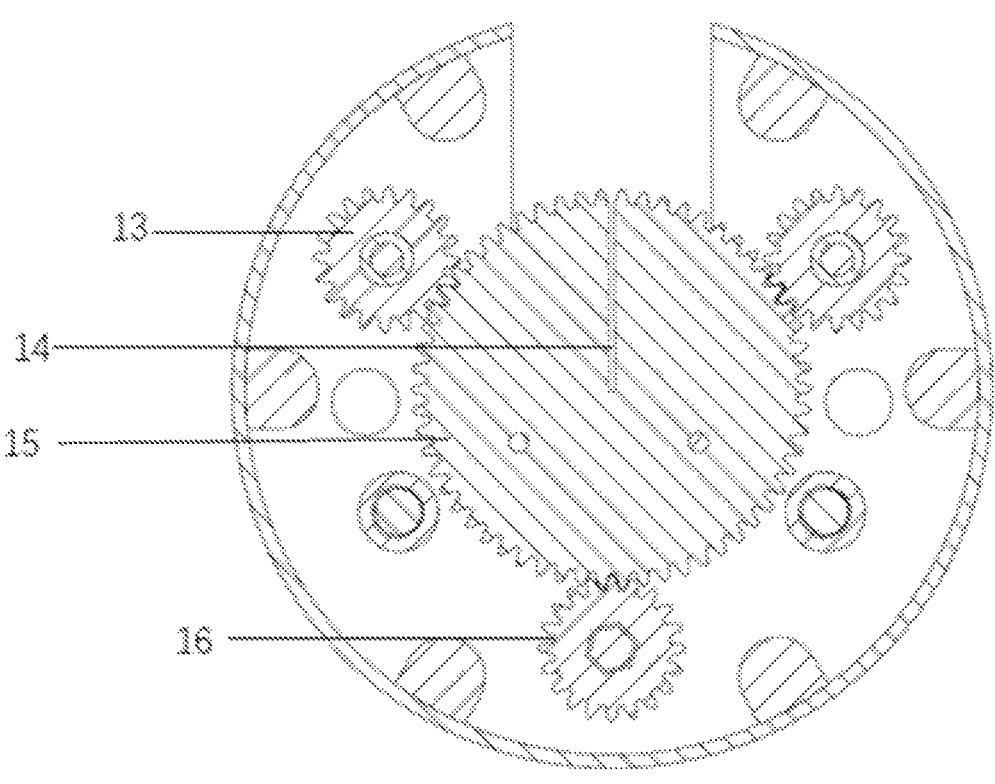
FIG. 5 is a cross-sectional view taken along the B-B section of FIG. 3.
Figure 6:
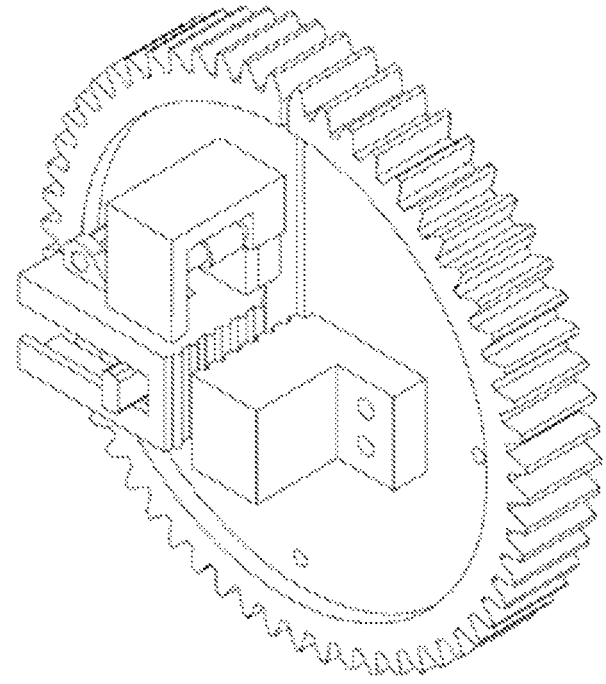
FIG. 6 is a perspective view of a sun gear with a locking device according to an example of the present invention.
Figure 7:
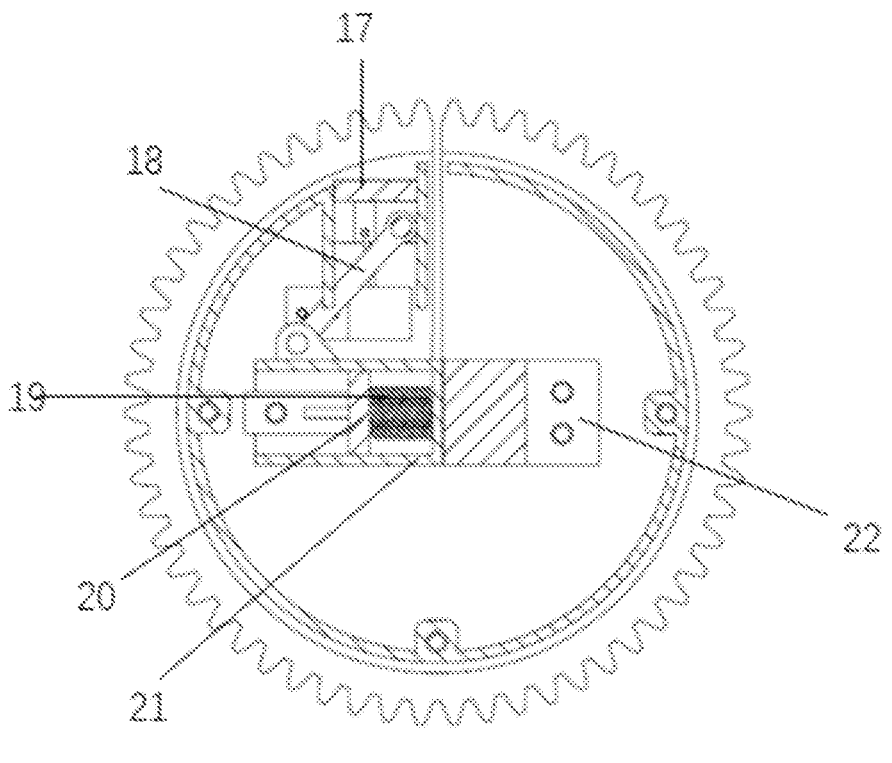
FIG. 7 is a cross-sectional view of the locking device according to an example of the present invention, in which the locking device is in a locked state.
Figure 8:
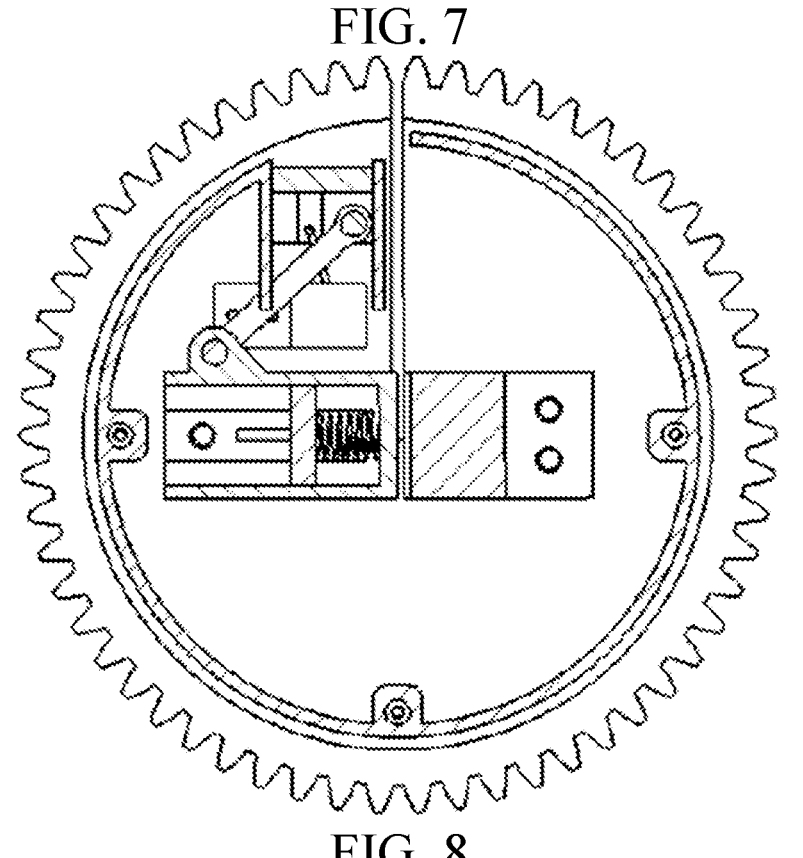
FIG. 8 is a cross-sectional view of the locking device according to an example of the present invention, in which the locking device is in a loosened state.
Figure 9:
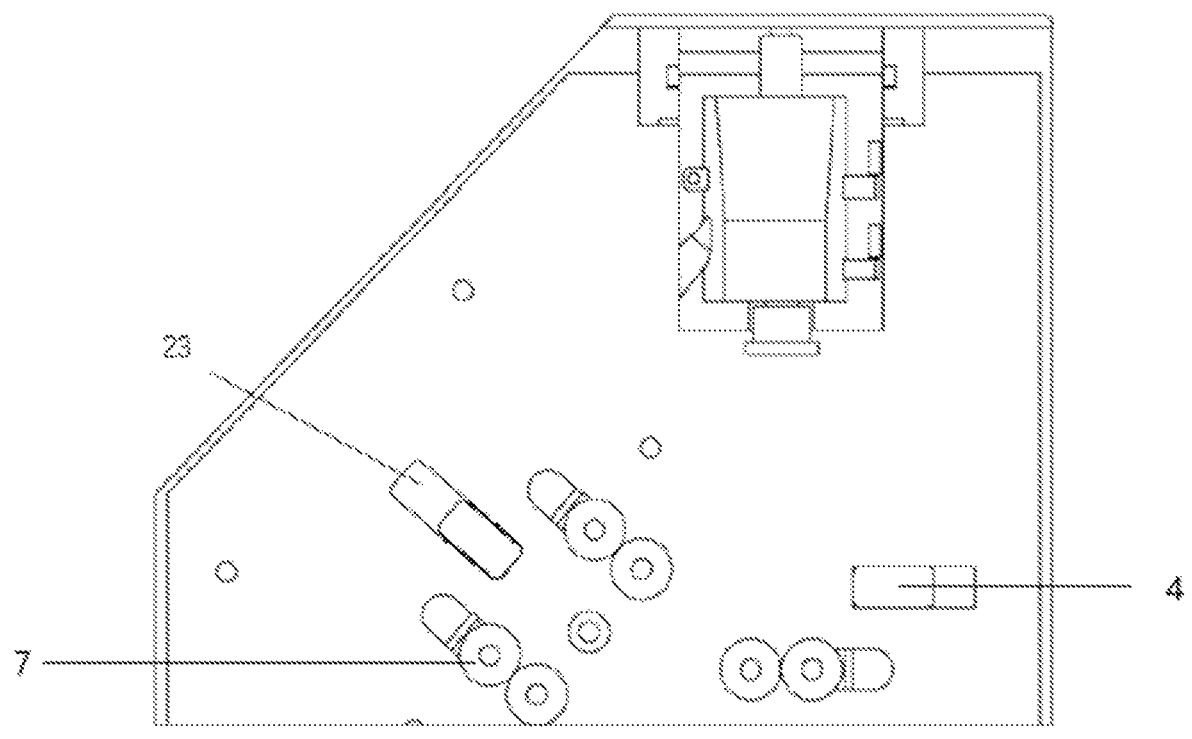
FIG. 9 is a top view of a transmission wheel in a locked state according to an example of the present invention.
Figure 10:
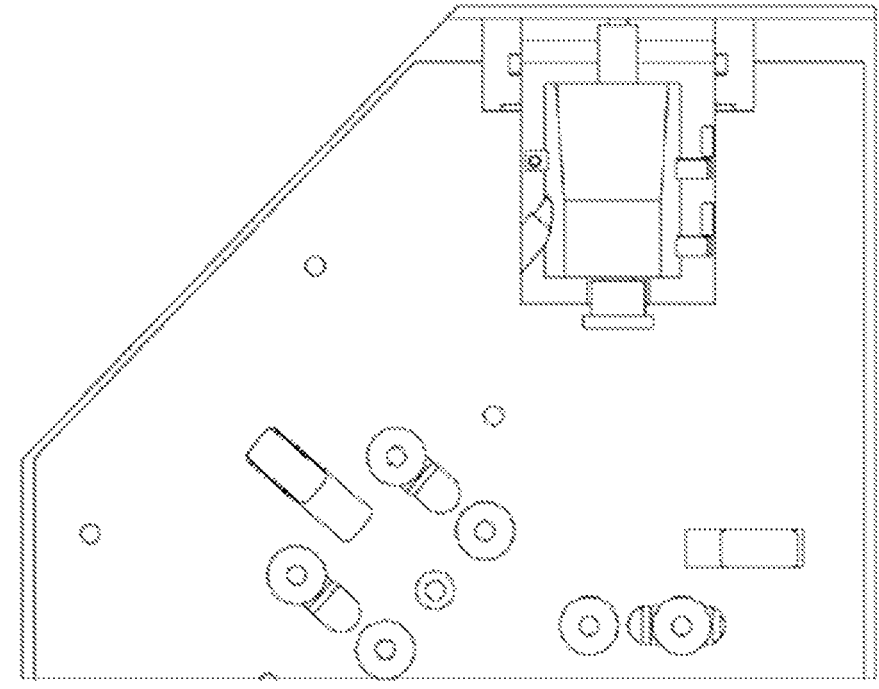
FIG. 10 is a top view of the transmission wheel in FIG. 9 in a loosened state.
Figure 11:
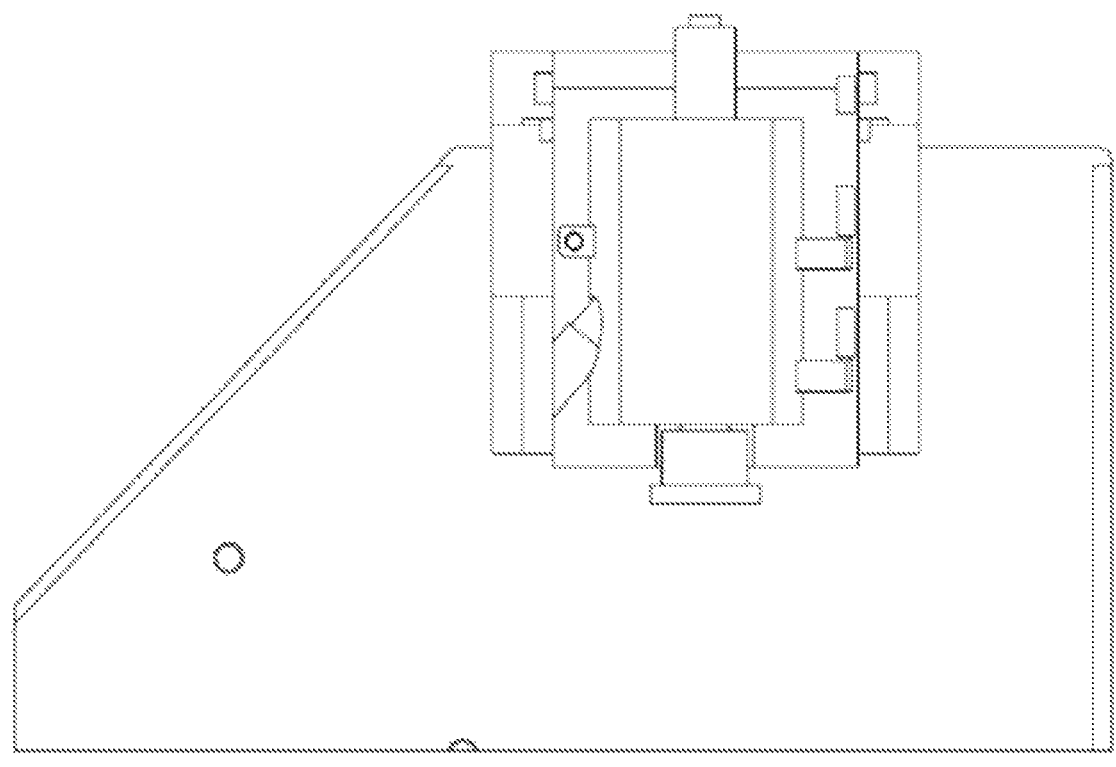
FIG. 11 is a top view of a Y-typed assembly in the forward position according to an example of the present invention.
Figure 12:
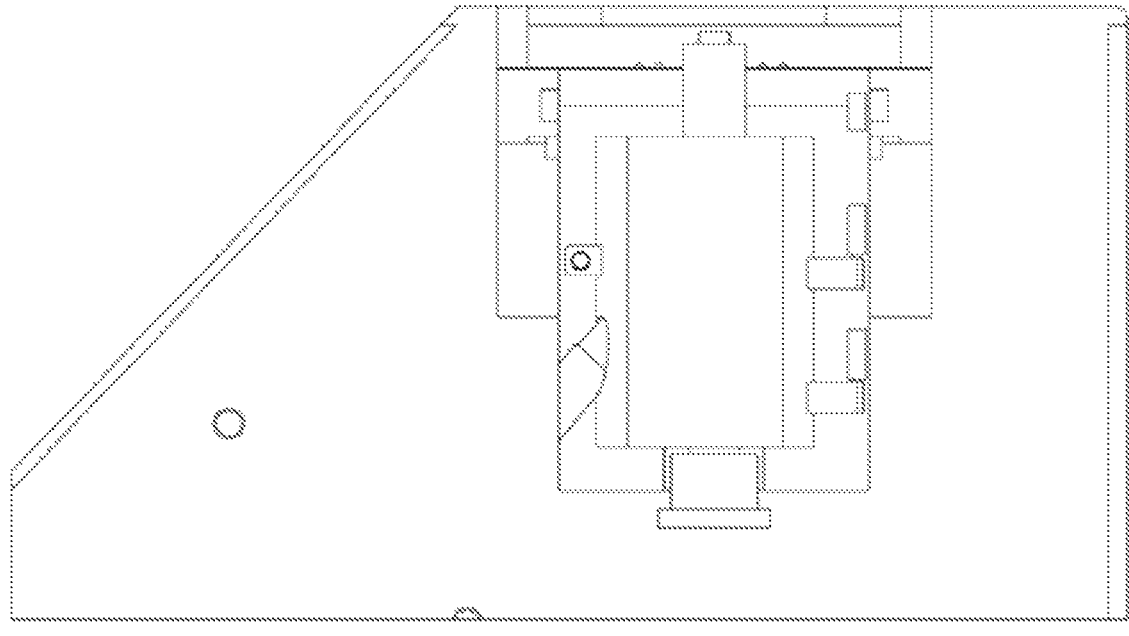
FIG. 12 is the top view of the Y-typed assembly in FIG. 11 in the retracement position.
Figure 13:
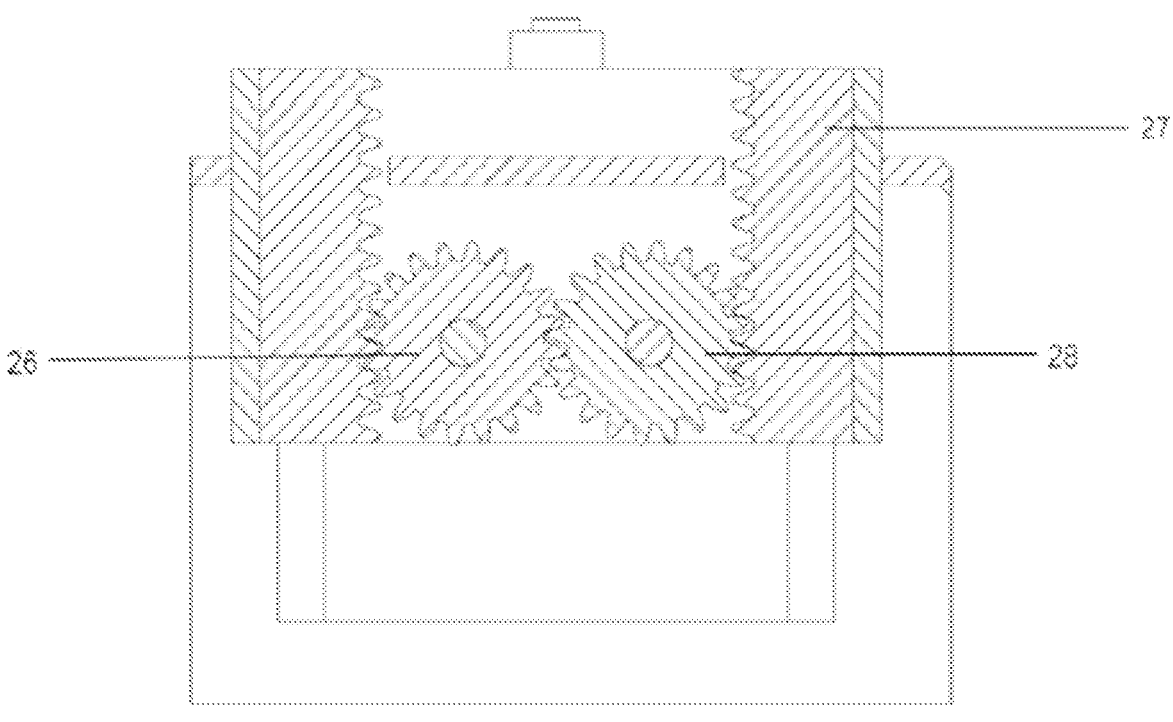
FIG. 13 is a schematic diagram of the motion mechanism of the Y-typed assembly according to an example of the present invention.
Figure 14:
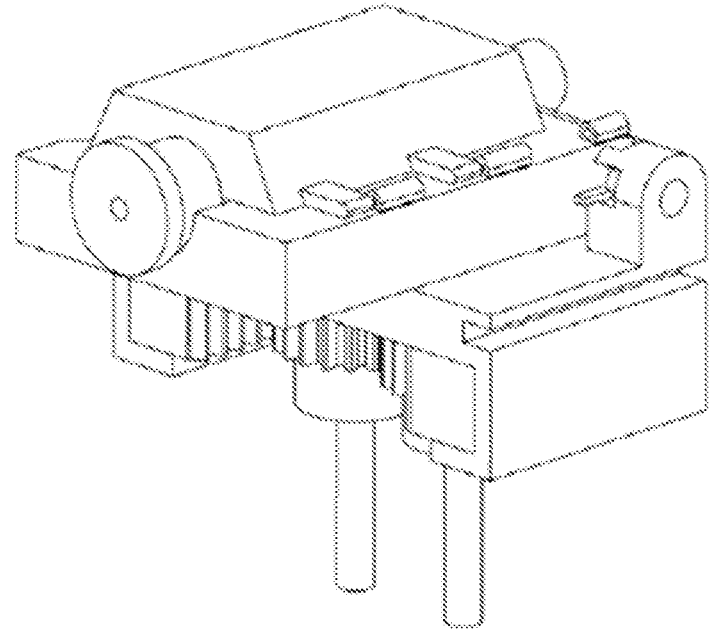
FIG. 14 is a perspective view of the Y-typed assembly according to an example of the present invention.
Figure 15:
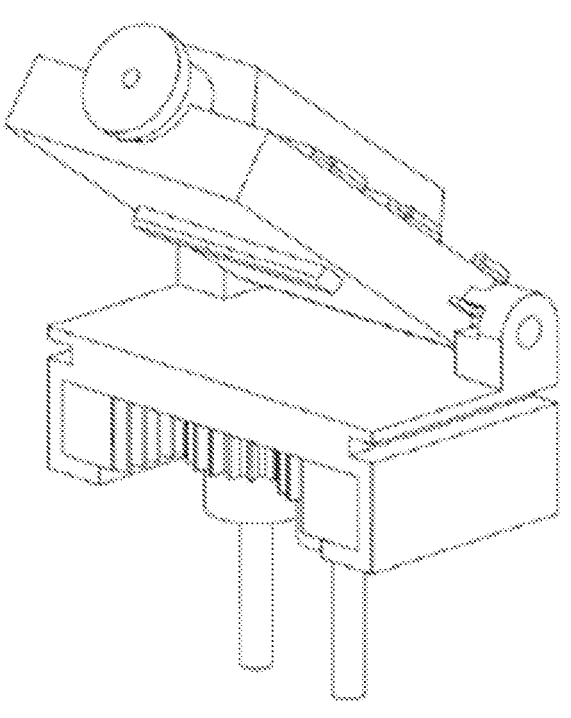
FIG. 15 is a perspective view of the Y-typed assembly in FIG. 14 in a raised state.
Figure 16:
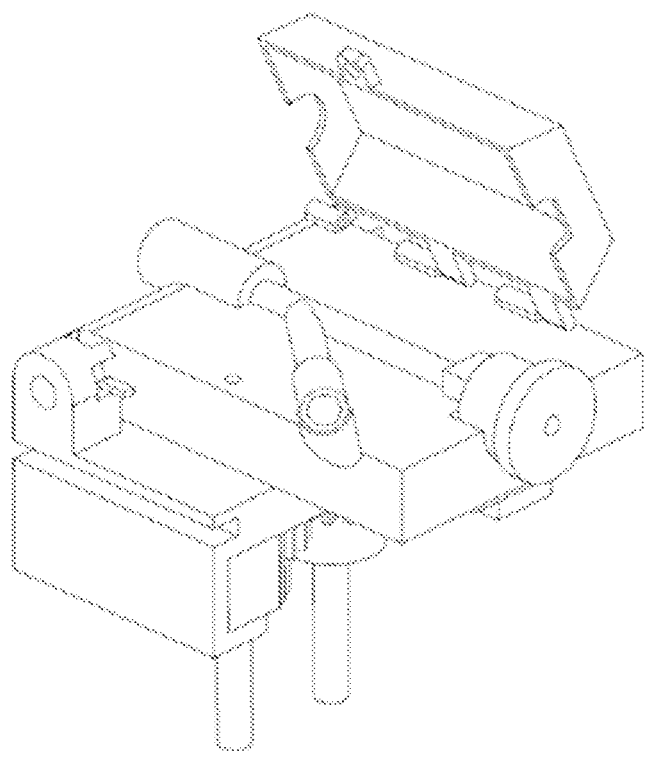
FIG. 16 is a perspective view of the Y-typed assembly in FIG. 14 in an open state.
Figure 17:
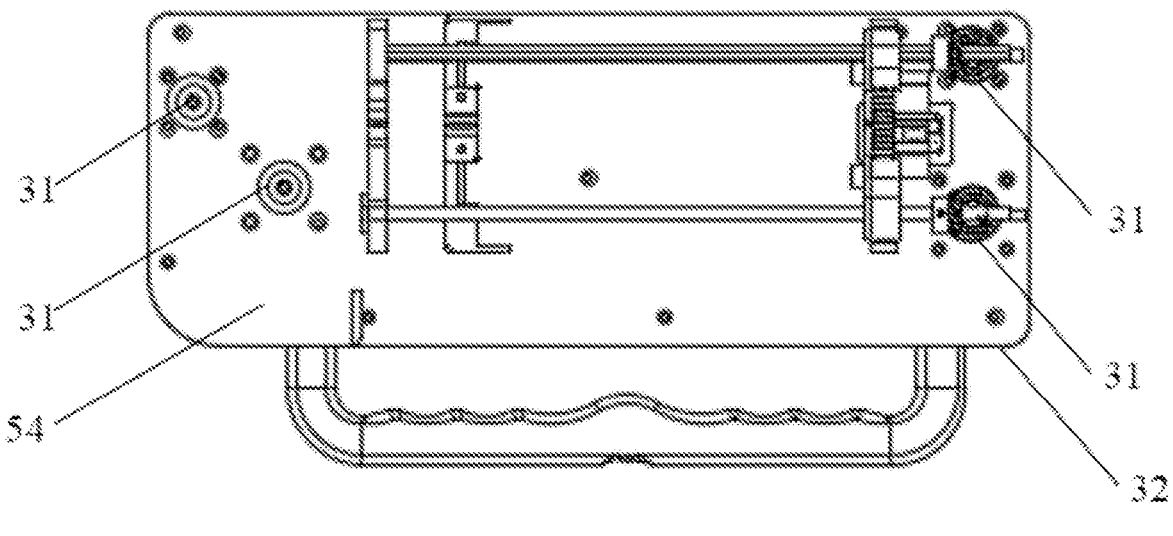
FIG. 17 is a top view of a terminal execution system according to an example of the present invention.
Figure 18:
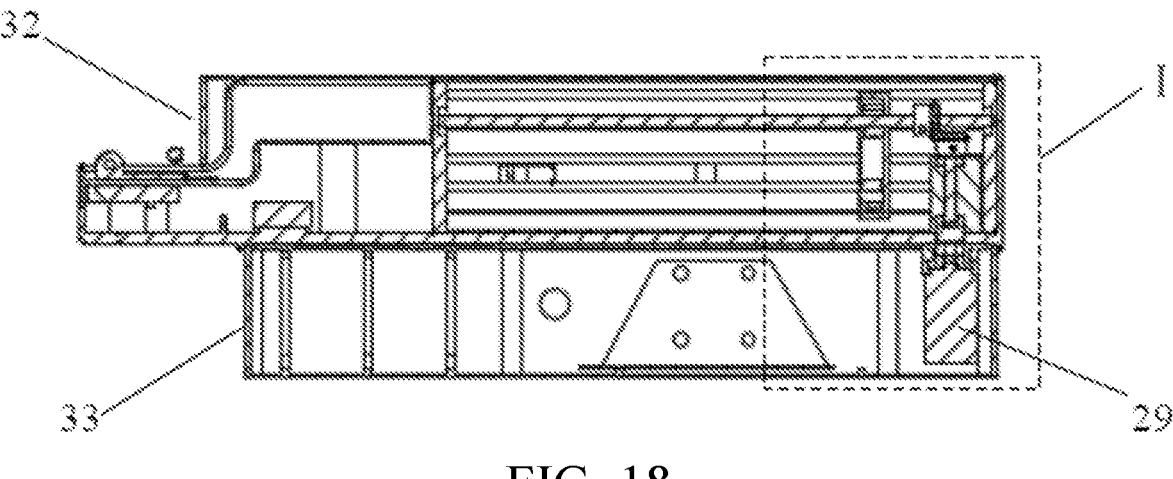
FIG. 18 is a cross-sectional view of the terminal actuation system in FIG. 17.

1—Guide wire transmission wheel; 2—Transmission screw rod; 3—Wheel set; 4—Guide wire transmission wheel locker; 5—Traveling wheel set; 6—Y-typed assembly; 7—Transmission wheel set; 8—Rotating shaft; 9—Pulley; 10—Fixed disk; 11—Rotating bevel gear; 12—Linkage belt; 13—Fixed gear; 14—Wire slot; 15—Sun gear; 16—Planet gear; 17—Key; 18—Linkage rod; 19—Spring; 20—Limit block; 21—Active member; 22—Fixed part; 23—Transmission wheel set locking switch; 24—Fixed plate;

25—Guide wire supporting rod; 26—Driving gear; 27—Rack; 28—Driven gear; 29—Motor; 30—First magnetic induction coupling; 31—Second magnetic induction coupling; 32—Execution housing; 33—Driving housing; 34—Rotating wheel set; 35—Magnetic induction coupling set; 36—Locking device; 37—First sensing point; 38—First inductor; 39—Second sensing point; 40—Second inductor; 41—Sensor opening; 42—Guide wire supporting sliding rod; 43—Embedded groove; 44—Round through hole; 45—Guide wire control module; 46—Guide wire center holder; 47—Guide wire locker; 48—Upper part; 49—Lower part; 50—Magnet; 51—Guide wire hole; 52—Guide wire locking knob; 53—Space layer; 54—Terminal execution system; 55—Surgical robot arm; 56—Remote microcomputer control end; 57—Single gear; 58—First tooth edge; 59—Second straight edge; 60—Third connecting edge; 61—Moving magnetic member; 62—Fixed magnetic member; 63—Y-typed valve; 64—Tray; 65—Smooth axis; 66—Worm; 67—Support rail; 68—Sliding sleeve; 69—Sliding sleeve handle; 70—Sliding sleeve track; 71—Guide catheter; 72—Intermediate connector.

DETAILED DESCRIPTION

After extensive and in-depth research and through a large number of screening, the inventors have developed a surgical robot system for the first time. Compared with the prior art, the system of the present application performs interventional surgery by remotely operating a robot to realize remote control the advance, retreat and rotation of the guide wire and guide catheter during surgery, and can also control the advance and retreat of the balloon catheter or stent catheter at the same time. The terminal execution system is divided into the upper execution housing and the lower drive housing through the non-contact motor system. The execution housing is used to accommodate the module components of various interventional devices for one-time use, and the drive housing is used to accommodate non-sterilizing and non-cleaning power components and control components. A space gap is formed between the execution housing and the drive housing to place sterile cloth to block the pollution to the non-sterilizing and non-cleaning components in the drive housing, so as not to affect the normal operation of the vascular interventional robot. The positioner assembly is provided with the first inductor and the first sensing point for positioning the axial position of the sun gear, and the second inductor and the second sensing point for positioning the radial position of the sun gear. This allows the position and angle of the sun gear to be effectively determined, thereby facilitating the adjustments of the distance in and out and the angle of rotation of the intervention device. The driving components such as the motor, the transmission screw rod, etc. are moved into the drive housing, this reduces the occupation of the space in the execution housing, so that there is more space for the assembly and operation of interventional devices in the execution housing, and it is convenient to clean the execution housing. In addition, a positioning device for the surgical robot arm is provided to ensure that the surgical robot arm remains stationary when the execution housing is mounted on the drive housing (i.e. the execution housing is located on top of the drive housing), so that its movement does not adversely affect the surgery and the safety of the robot is improved. The present invention combines a variety of interventional surgical consumables in one system, wherein the mechanical brake is mainly realized by meshing between gears or transmission through transmission rod(s). The present invention realizes the robotization of interventional surgery and avoids the operator being exposed to a large number of radiation injuries during the surgery. At the same time, the robotization of interventional surgery improves the stability and accuracy of the surgery. Further, the operator can remotely control, reducing the risk of cross-infection between doctors and patients. The present invention is completed on these bases.

The present invention is further described below in conjunction with specific embodiments. It should be understood that these examples are intended to illustrate the invention only and not to limit the scope of the invention. Furthermore, the drawings are schematic diagrams, and therefore the apparatus and device of the present invention are not limited by the size or scale of the schematic diagrams.

It should be noted that in the claims and specification of the present patent, relational terms such as first and second, etc. are only used to distinguish one entity or operation from another entity or operation, and do not necessarily require or imply that there is any such actual relationship or order between these entities or operations. Moreover, the terms "comprise", "include" or any other variant thereof are intended to cover non-exclusive inclusions such that a process, method, article or device comprising a series of elements comprises not only those elements, but also other elements not explicitly listed, or also elements inherent to such process, method, article or device. In the absence of further restrictions, the element defined by the statement "include a/an" do not exclude the existence of other identical elements in the process, method, article or device including the element.

Example 1

The surgical robot system of this Example is shown in FIGS. 1a-16. The surgical robot system comprises a remote microcomputer control end 56, a surgical robot arm 55 and a terminal execution system 54. The terminal execution system 54 includes a guide wire control module, a balloon/stent control module, and a guide catheter control module, which can control the advance, retreat, and rotation of a guide wire, as well as the advance, retreat, and rotation of the balloon catheter or stent catheter and the guide catheter. Among them, the guide wire control module includes a rotating assembly and a traveling assembly.

The rotating assembly is used to control the rotation of the guide wire. The rotating assembly includes a rotating wheel set, a rotating shaft 8 concentrically connected to the rotating wheel set, a planet gear 16 sleeved on the rotating shaft 8 and slidable relative to the rotating shaft 8, and a sun gear 15 meshing with the planet gear 16. The sun gear 15 is provided with a wire slot 14 for embedding the guide wire. The wire slot 14 is tapering along the radius from outside to inside for embedding guide wires of different diameters. The wire slot 14 is opened at the bottom of the valley between the teeth of the sun gear 15, which does not affect the meshing between the sun gear 15 and other gears. The wire slot 14 opens from the valley between the teeth of the sun gear 15 to the center of the circle of the sun gear 15. The wire slot 14 is used to insert the guide wire and ensure the coaxial rotation of the guide wire. The rotation shaft 8 is a hexagonal axis.

The traveling assembly is used to control the advance or retreat of the guide wire. The traveling assembly includes traveling (advancing) wheel set 5, transmission screw rods 2 concentrically connected to the gears of the traveling wheel set 5, and a fixed disk 10 for supporting the sun gear 15. The sun gear 15 and the planet gear 16 are both placed in the inner cavity of the fixed disk 10 and move with the forward and backward movement of the fixed disk 10. The proximal end of the transmission screw rod 2 is connected and fixed with a traveling bevel gear 11 of the traveling wheel set 5. The proximal end of the rotating shaft 8 is connected and fixed with the rotating wheel set. Both the distal end of the transmission screw rod 2 and the distal end of the rotating shaft 8 are fixed to the fixed plate 24 located at the distal end by means of bearings. A wire slot is provided on the fixed plate 24 to allow the insertion of the guide wire. The traveling wheel set 5 consists of two sets of traveling bevel gear sets. The traveling wheel set 5 also includes a linkage belt 12 for connecting the traveling bevel gears 11, and the linkage between the traveling bevel gears 11 of the traveling wheel set 5 is realized by the linkage belt 12. The fixed disk 10 is a hollow disk, and the sun gear 15 is placed in the hollow cavity of the fixed disk 10. The fixed disk 10 is also provided with a radial opening for embedding the guide wire. The sun gear 15 and the fixed disk 10 are concentrically aligned.

The rotating wheel set and the traveling wheel set 5 are both on the same section. The rotating wheel set and the traveling wheel set 5 are both driven by motor(s). The rotation of the rotating wheel set drives the rotating shaft 8, which is concentrically connected to it, to rotate together. The rotating shaft 8 drives the planet gear 16 to rotate. The planet gear 16 drives the sun gear 15 to rotate through meshing effect.

The rotation of the gears of the traveling wheel set 5 drives the transmission screw rods 2 to rotate. The fixed disk 10 is in threaded meshing connection with the transmission screw rods 2, and advances or retreats with the rotation of the transmission screw rods 2.

At least two fixed gears 13 are provided on the fixed disk 10, and the fixed gears 13 are meshed with the sun gear 15 for fixing the sun gear 15. The fixed gears 13 are symmetrically disposed on the upper part of the fixed disk 10 to provide symmetrical supporting forces for the sun gear 15 and clamping forces corresponding to the rotating shafts 8.

Among them, the combination of the sun gear 15, the fixed gears 13, the planet gear 16 and the fixed disk 10 is referred to as the wheel set 3.

The guide wire control module includes a locking device for locking the guide wire, and the locking device is fixed to the sun gear 15. The locking device comprises a locking control assembly, an active member 21, and a fixing member 22. The fixing member 22 is fixed to the sun gear 15 and aligned with one side of the wire slot 14. The active member 21 is disposed relative to the fixing member 22 and aligned with the other side of the wire slot 14. The locking control assembly is connected to the active member 21 for controlling the positional relationship of the active member 21 relative to the fixing member 22. The locking control assembly controls the active member 21 away from the fixed member 22, i.e. the wire slot 14 forms a passage that can be embedded in the guide wire. The locking control assembly controls the active member 21 against the fixed member 22 to clamp the guide wire embedded in the wire slot 14. The locking device can be driven electrically or pneumatically.

The locking control assembly includes a key 17, a linkage rod 18, a spring 19 and a limit block 20. The spring 19 and the limit block 20 are arranged in the inner cavity of the active member 21. The limit block 20 is fixed. The spring 19 is located between the limit block 20 and the side wall of the active member 21. One end of the linkage rod 18 is connected with the key 17, and the other end of the linkage rod 18 is connected with the active member 21. When the locking device is in the loosened state, by pressing the key 17, the linkage rod 18 is driven to move outward, thereby driving the active member 21 to move radially outward and the active member 21 is moved away from the fixed member 22, and at this time, the spring 19 is in a compressed state. When the locking device is in the locked state, the pressing control of the key 17 is released, and under the action of the elastic force of the spring 19, the active member 21 moves radially inward and abuts against the fixed member 22, and the key 17 returns to the initial position.

The contact surfaces between the active member 21 and the fixed member 22 are toothed clamping surfaces to provide a greater clamping force to the guide wire.

The guide wire control module includes a guide wire supporting rod disposed between the sun gear 15 and the fixed plate 24. The guide wire supporting rod is slidable along the axial direction of the guide wire.

The guide wire supporting rod includes a supporting frame 25 and pulleys 9 on both sides. The supporting frame 25 is provided with a wire slot corresponding to the wire slots on the sun gear 15 and the fixed plate 24. In the use state, the guide wire is embedded in the wire slot, and the pulleys 9 on both sides can move in the corresponding sliding grooves on the two side walls, respectively.

The sliding grooves start at the two side wall surfaces corresponding to the middle section of the sun gear 15 and the fixed plate 24, and ends at the two side wall surfaces corresponding to the fixed plate 24.

The sliding grooves start at the two side wall surfaces corresponding to the sun gear 15 and ends at the two side wall surfaces corresponding to the fixed plate 24. A stop member(s) is provided on the sliding grooves corresponding to the middle section of the sun gear 15 and the fixed plate 24, and the stop member is used to block the sliding of the intermediate support member.

The guide wire supporting rod is provided with a magnet, and correspondingly, a wheel cover is provided with another magnet, and the two magnets are mutually attractive. In the operation of transporting the guide wire, the guide wire supporting rod is initially located in the middle section between the sun gear 15 and the fixed plate 24 and the guide wire is placed in the wire slot. As the fixed disk 10 moves distally along the transmission screw rod 2, the two magnets generate attraction, and the guide wire supporting rod continues to move distally together with the fixed disk 10. In the operation of retracting the guide wire, the guide wire supporting rod retracts to the proximal end together with the fixed disk 10, when retracted to the middle section between the sun gear 15 and the fixed plate 24, under the blocking effect of the stop member or the walls of the sliding grooves, the guide wire supporting rod is no longer retracted and is fixed, while the fixed plate 10 can continue to be retracted.

A pair of guide wire transmission wheels 1 are provided on the distal end side of the fixed plate 24 and at a distance of 5 mm to 15 mm from the fixed plate 24 (center distance) for supporting and transporting the guide wire at the distal end. The joint of the guide wire transmission wheels 1 corresponds to the wire slot on the fixed plate 24. The guide wire is placed between the guide wire transmission wheels 1, and the guide wire is transported by friction between the guide wire transmission wheels 1. The pair of guide wire transmission wheels 1 is equipped with a pair of guide wire transmission wheel lockers 4 for controlling a distance between the guide wire transmission wheels 1 and further controlling the locking condition of the guide wire transmission wheels 1.

The balloon/stent control module comprises a transmission wheel set 7 for controlling the advancement or retraction of the balloon or stent catheter. The transmission wheel set 7 includes two pairs of friction wheel sets, and a gear set connected below, and the gear is connected to the motor. When in use, the motor drives the gear to rotate, and the gear drives the upper friction wheel sets to rotate, and the balloon catheter or stent catheter clamped by the friction wheel sets advances or retreats accordingly. The transmission wheel set 7 is also equipped with a pair of transmission wheel set locking switches 23, which are used to control the distance between a pair of friction wheels and further control the locking condition of the transmission wheel set 7.

The guide catheter control module comprises a Y-typed assembly 6, which is a Y-typed combination for a guide wire (not shown) and a guide catheter (not shown). The Y-typed assembly 6 is movable, and the movement of the Y-typed assembly 6 can deliver or retract the guide catheter. The Y-typed assembly 6 is provided at the distal end of the system, which is moved back and forth by the engagement of the gears (26, 28) and the rack 27. Among them, the Y-typed assembly 6 is fixedly connected with the rack 27, the driving gear 26 is connected with the motor, the driving gear 26 drives the driven gear 28 to rotate through the mutual meshing between the gears, and the gears (26, 28) and the rack 27 mesh with each other. When in use, the motor drives the driving gear 26 to rotate, and under the action of meshing, the rack 27 moves forward or backward, thereby driving the Y-typed assembly 6 forward or backward.

The operator remotely controls the movement of the guide wire control module, the balloon/stent control module and the guide catheter module using signal transmission through the remote microcomputer control end 56. It should be noted that the front end of the Y-typed valve (Y-typed assembly 6) is connected to the guide catheter, and the forward and backward movement of the guide catheter is controlled by controlling the forward and backward movement of the Y-typed valve. The transmission wheel set 7 clamps the balloon catheter or the stent balloon catheter forward or backward. The rotating wheel set and the traveling wheel set 5 control the rotation, forward or backward of the guide wire. The rotation, forward or backward of all components can be done by the operator controlling the terminal controller outside the operating room. The system communicates with the operating terminal through wired, wireless (WiFi, Bluetooth, etc.) or the Internet. The operation terminal is a computer, including a joystick and a tablet computer. The operator adjusts the forward or backward distance of the guide wire and the rotation angle of the guide wire, adjusts the forward or backward distance of the guide catheter, and adjusts the forward or backward distance of the balloon catheter or the stent catheter by adjusting the parameters displayed on the tablet computer, and then operates the joystick to control the forward, backward or rotating of the guide wire, the forward or backward of the balloon catheter or stent catheter, and the forward, backward or rotating of the guide catheter.

It should be noted that there can be more than two wire slots 14 on the fixed plate 24. When two to three guide wires are used in the operation, the wire slots 14 are embedded in each of the guide wires.

The system is made of PC, nylon and other plastic materials or 304, 316 stainless steel and other metal materials, which are non-toxic to human body, can be disinfected and sterilized, and is low in price, suitable for one-time use.

Preferably, the system further comprises non-contact motor systems disposed on the terminal execution system 54 for providing a drive force for forward, backward and rotational movement of the interventional device, as shown in FIGS. 17-21.

The terminal execution system 54 includes an execution housing 32 loaded with mechanical components for driving forward, backward, and rotational movement of the interventional device, and a driving housing 33 loaded with electrically powered components (e. g., including, but not limited to, power supplies and controls) for powering the mechanical components.

The non-contact motor system includes a motor 29 (the motor 29 is fixed in the driving housing 33), a first magnetic induction coupling 30 coupled to the motor 29 and driven by the motor 29, a second magnetic induction coupling 31 provided corresponding to the first magnetic induction coupling 30 (the second magnetic induction coupling 31 is fixed on the bottom wall of the execution housing 32), and a transmission gear(s) coupled to the second magnetic induction coupling 31. Wherein, the first magnetic induction coupling 30 and the second magnetic induction coupling 31 are coaxial with each other.

In this Example, the number of non-contact motor systems is four. The second magnetic induction coupling 31 can be connected to the traveling wheel set 5, the rotating wheel set 34, the transmission wheel set 7 and the rack and pinion group for the guide catheter through the transmission gear(s), respectively, and thus be driven to operate.

Under the support of the pair of first and second magnetic-induction couplings, a space layer having a thickness of 2 mm to 20 mm is formed between the actuator housing 32 and the driving housing 33. Due to the presence of this space layer, it is possible to lay a sterile cloth (e. g., a blood-isolating sterile cloth) between the execution housing 32 and the driving housing 33 for reducing contamination of components in the driving housing 33.

Figure 19:
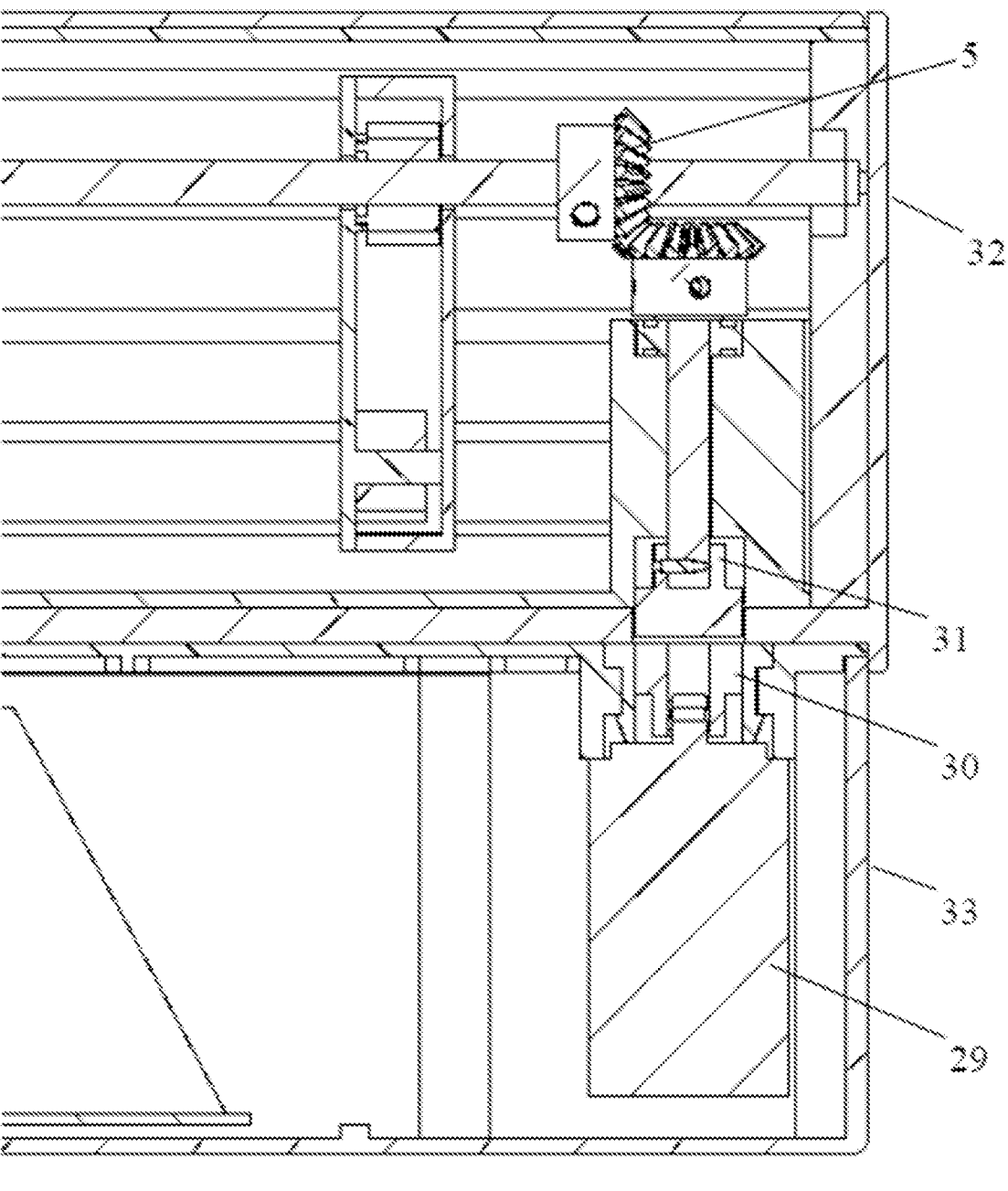
FIG. 19 is an enlarged view of part I in FIG. 18.
Figure 20:
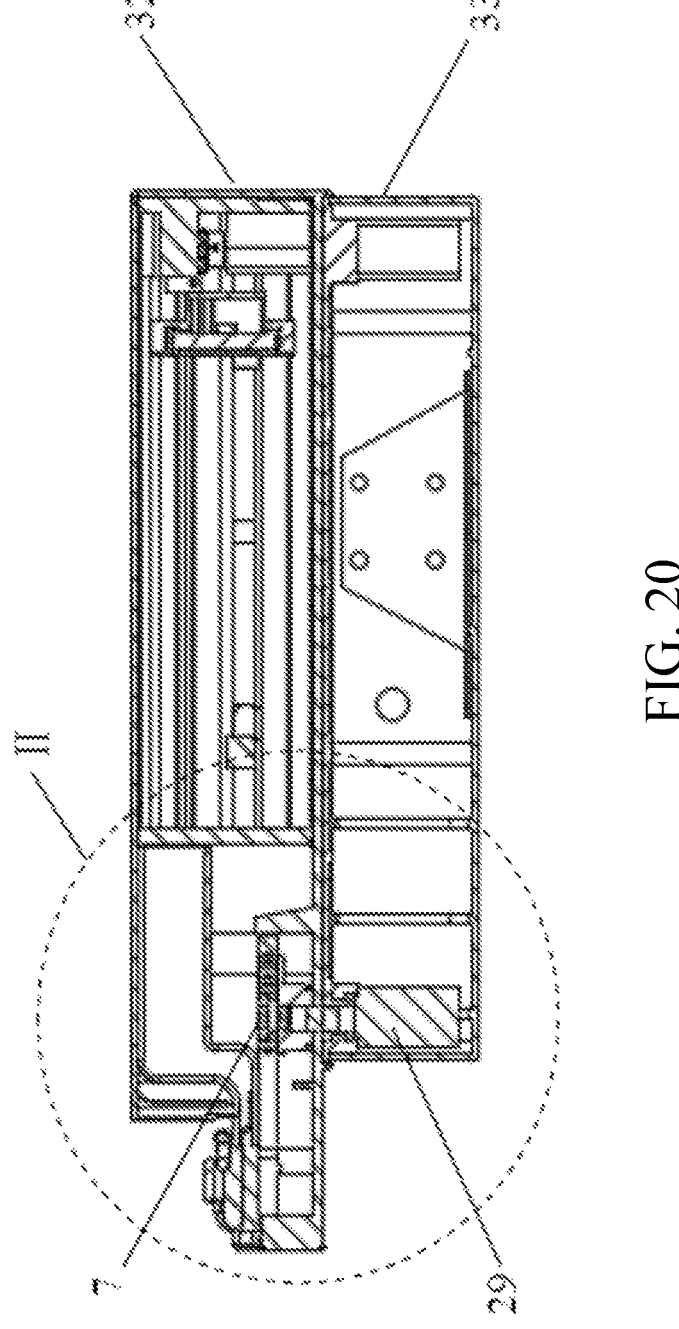
FIG. 20 is a front view of the terminal actuation system in FIG. 17.

The terminal execution system 54 includes a guide wire control module in the interventional device, the guide wire control module including a rotating assembly and a traveling assembly. The traveling assembly is used to control the advance and retreat of the guide wire; the rotating assembly is used to control the rotation of the guide wire. The rotating assembly includes a rotating wheel set, a rotating shaft concentrically connected with the rotating wheel set, a planet gear sleeved on the rotating shaft and slidable relative to the rotating shaft, and a sun gear meshing with the planet gear. There is a wire slot on the sun gear. The wire slot is opened (grooved) from the bottom of the valley between the teeth of the sun gear to the center of the circle of the sun gear. The wire slot is used to insert (embed) the guide wire and ensure the coaxiality of the rotation of the guide wire. The traveling assembly includes a traveling wheel set, a transmission screw rod concentrically connected to bevel gear(s) of the traveling wheel set, and a fixed disk for supporting the sun gear. Wherein, the rotating wheel set and the traveling wheel set are both driven by the above non-contact motor system(s). Among them, the rotating wheel set 34, the traveling wheel set 5, and the transmission gears that engages with both are bevel gear sets, as shown in FIG. 19.

Figure 21:
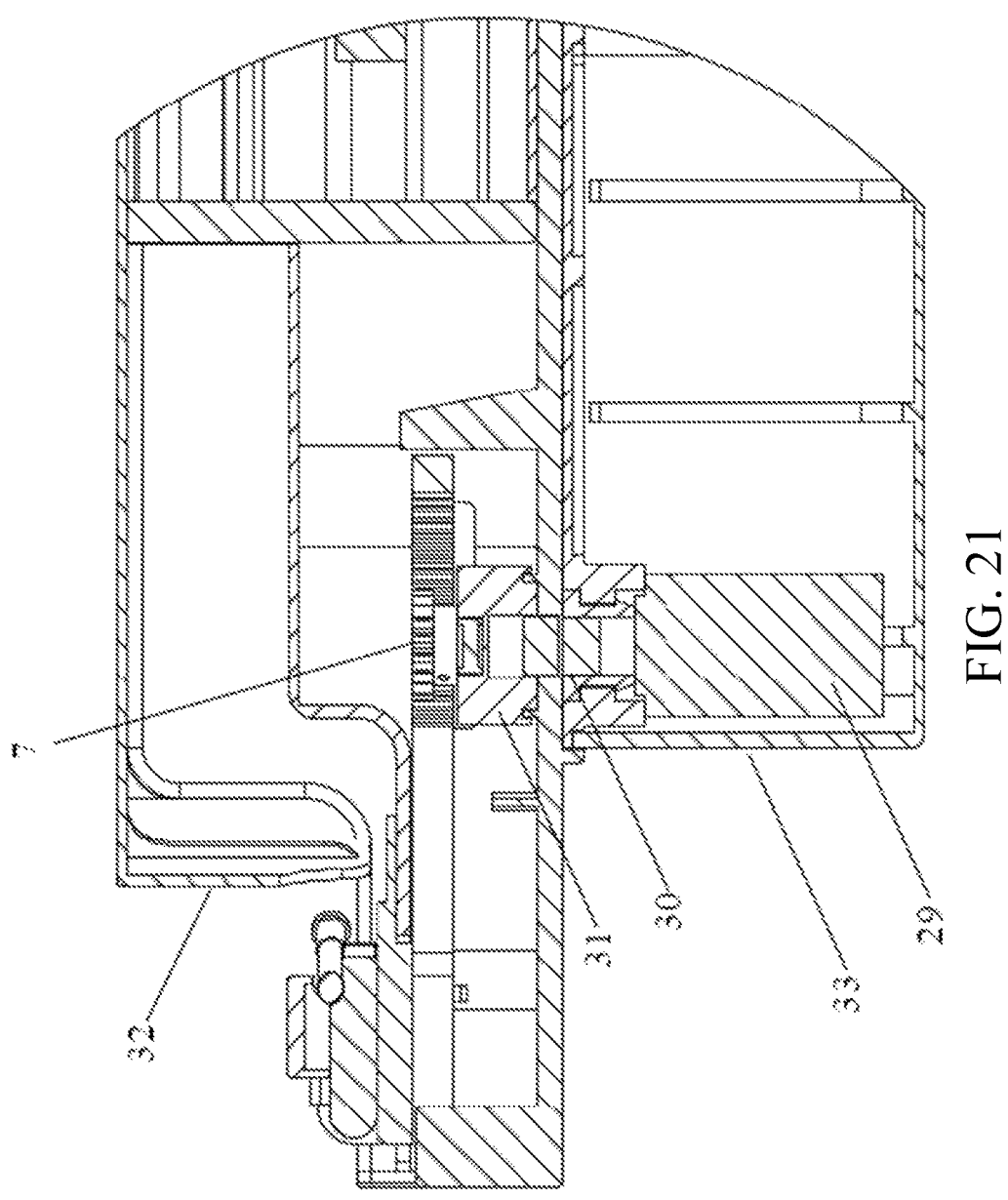
FIG. 21 is an enlarged view of part II in FIG. 20.
Figure 22:
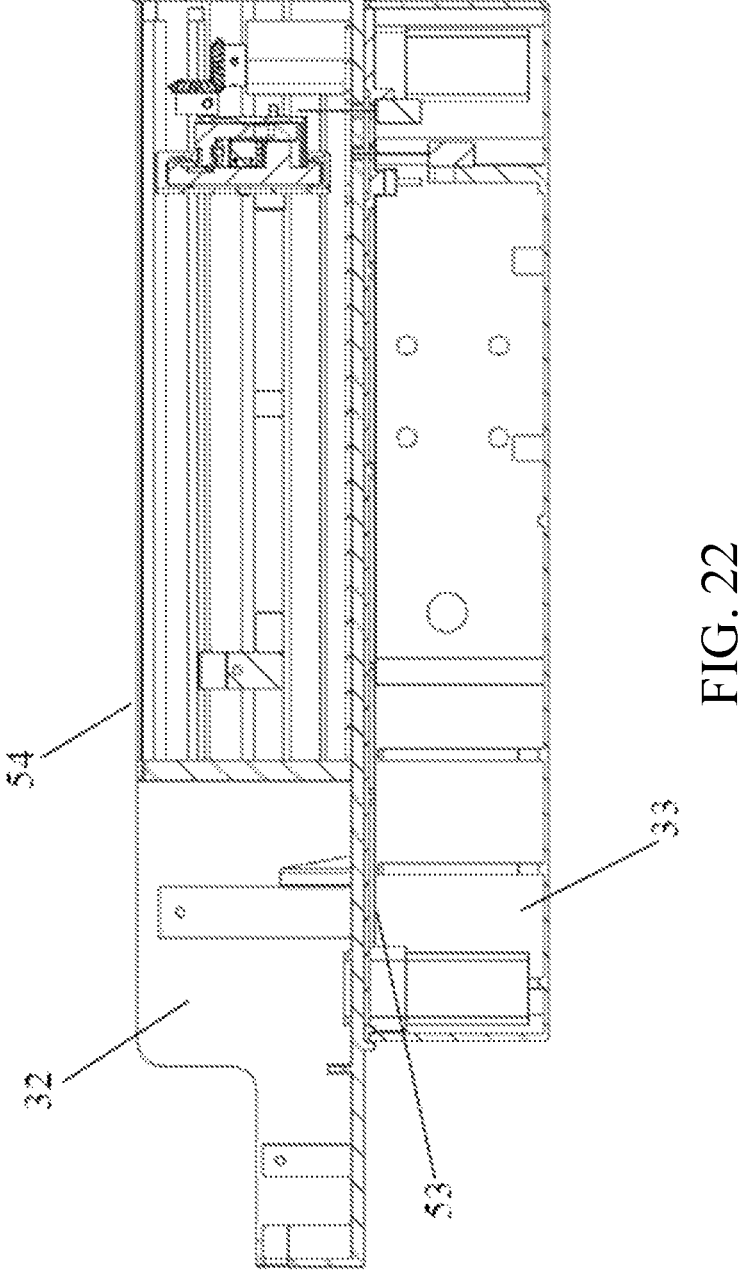
FIG. 22 is a cross-sectional view of the terminal execution system according to an example of the present invention.
Figure 23:
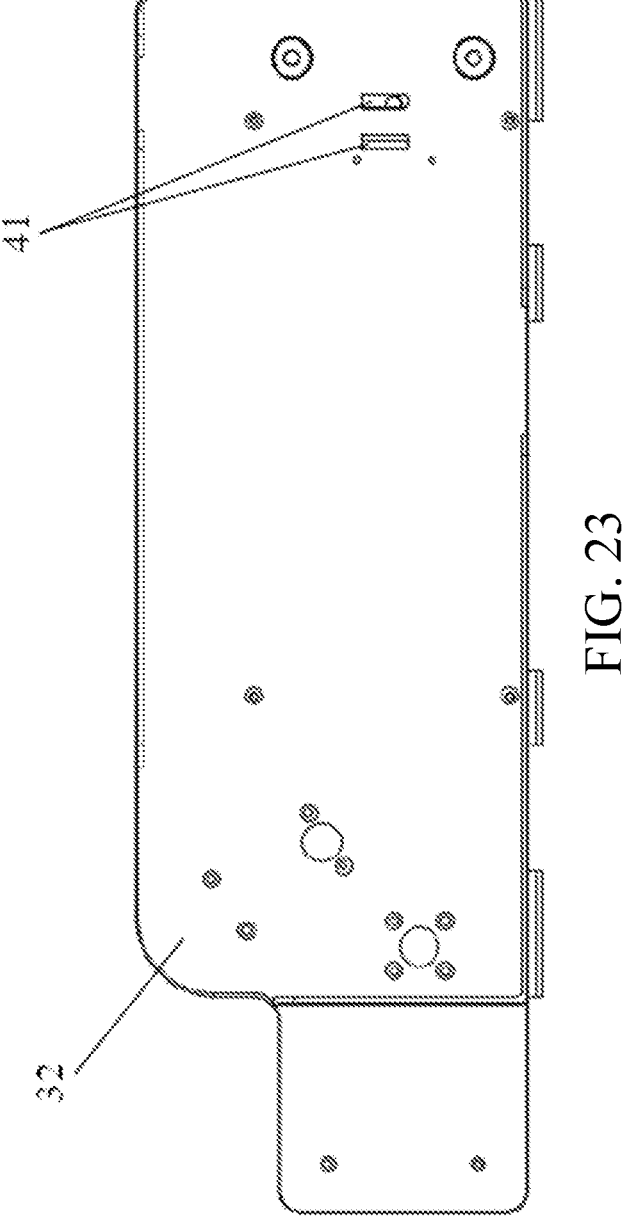
FIG. 23 is a top view of a driving housing of the terminal execution system in FIG. 22.
Figure 24:
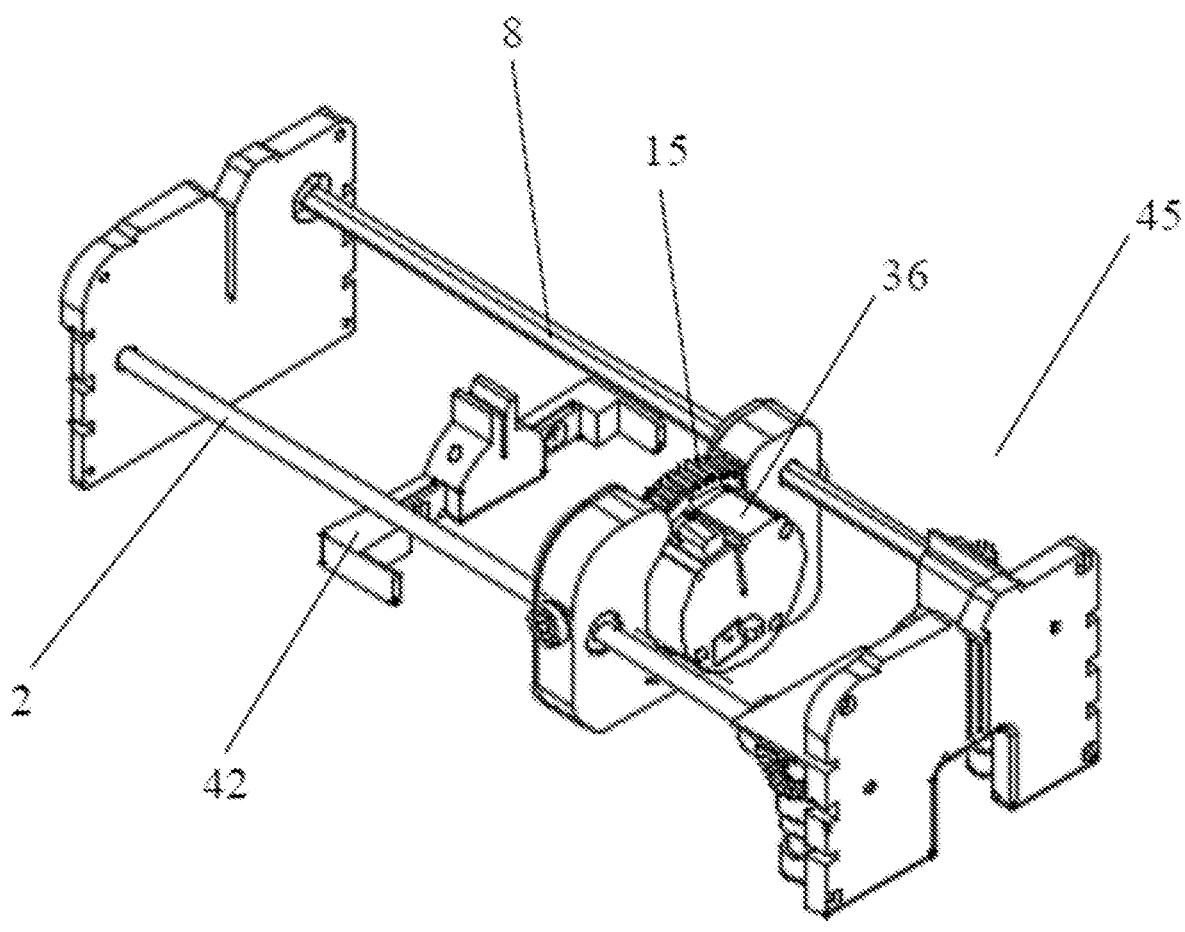
FIG. 24 is a perspective view of a guide wire control module of the terminal execution system according to an example of the present invention.
Figure 25:
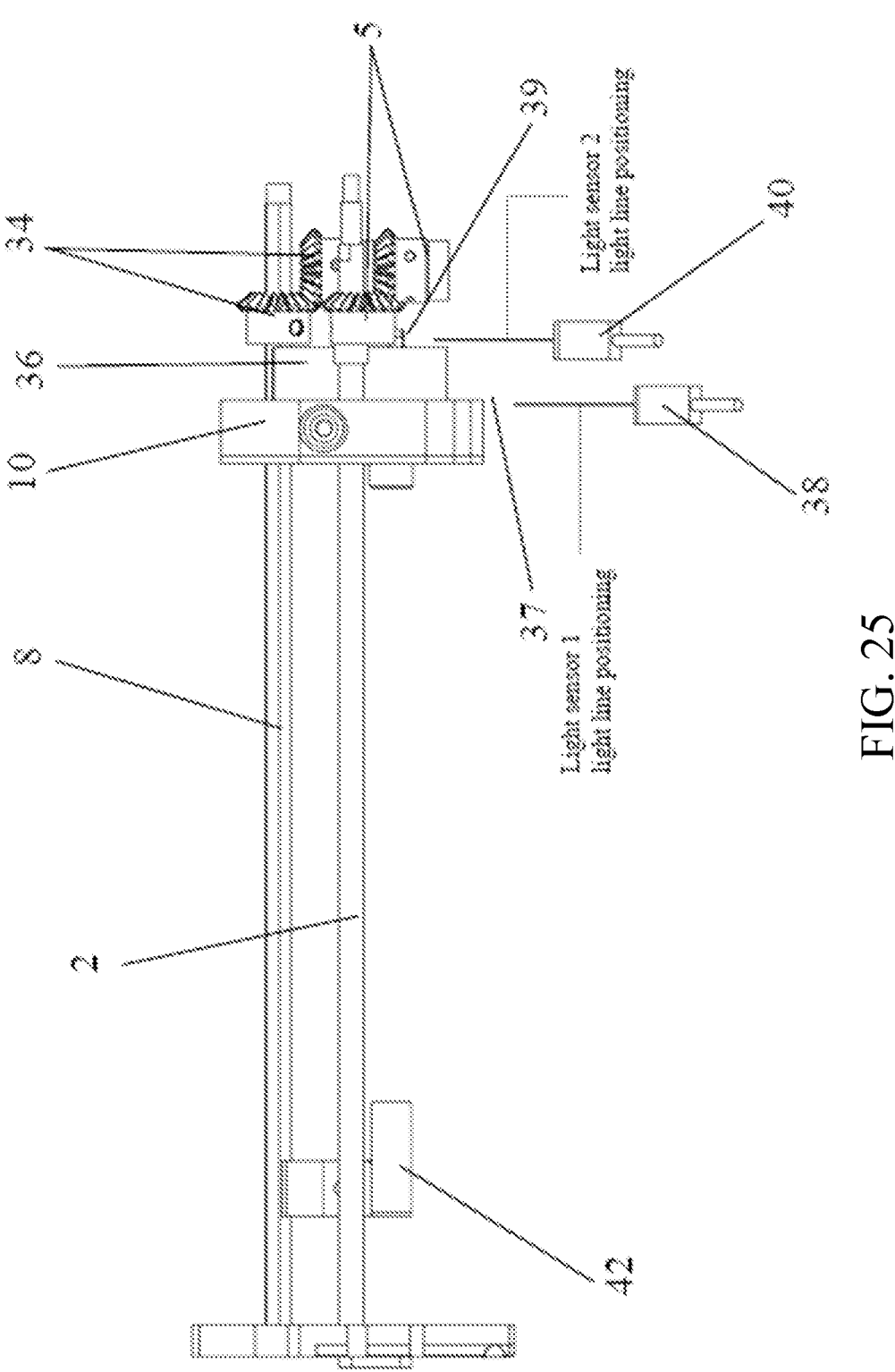
FIG. 25 is a front view of the guide wire control module of the terminal execution system in FIG. 24, and in which two control module locators are schematically illustrated.

The terminal execution system 54 includes a balloon/stent control module in the interventional device. The balloon/stent control module is used to control the advancement or retraction of the balloon catheter or stent catheter. The balloon/stent control module includes a transmission wheel assembly. The transmission wheel assembly includes a friction wheel set(s). Under the friction wheel set, there are friction wheel set gears meshing with each other. The friction wheel set clamps the balloon catheter or the stent catheter forward or backward. The terminal execution system 54 also includes a guide catheter control module in the interventional device. The guide conduit control module is used to control the advance or retraction of the guide catheter. The guide catheter control module includes a Y-typed assembly. The Y-typed assembly includes an upper Y-typed valve and a lower rack and pinion group. A distal port of the Y-typed valve is connected to the guide catheter, and a proximal port is penetrated the guide wire. The guide wire enters the guide catheter through the Y-typed valve and reaches the surgical site along the lumen of the guide catheter. The rack and pinion group drives the Y-typed assembly forward or backward, thereby driving the guide catheter forward or backward. Among them, the friction wheel set and the rack and pinion set are both driven by a non-contact motor system, wherein the transmission wheel set 7 is a spur gear set, as shown in FIG. 21.

The terminal execution system 54 is fixed on the end of the surgical robot arm 55 and moves with the surgical robot arm 55. The remote microcomputer control end 56 controls the movement of the surgical robot arm 55 and the movement inside the terminal execution system 54.

As shown in FIGS. 22-25, the terminal execution system 54 includes an execution housing 32 and a driving housing 33, wherein the execution housing 32 is loaded with mechanical components for performing transportation, withdrawal and rotation of interventional device, and the driving housing 33 is loaded with electrically powered components for providing driving power to the mechanical components. The execution housing 32 and the driving housing 33 are connected in a spatial distance through a magnetic induction coupling set 35, forming a space layer 53 with a gap of 2 mm to 20 mm between the execution housing 32 and the driving housing 33.

The terminal execution system 54 includes a guide wire control module 45 for controlling advance, retreat and rotation of the guide wire. The guide wire control module 45 includes a rotating assembly for controlling the rotation of the guide wire and a traveling assembly for controlling the advance or retreat of the guide wire.

The rotating assembly includes a rotating wheel set 34, a rotating shaft 8 concentrically connected to the rotating wheel set 34, a planet gear sleeved on the rotating shaft 8 and slidable relative to the rotating shaft 8, and a sun gear 15 meshing with the planet gear. There is a wire slot on the sun gear. The wire slot is opened from the bottom of the valley between the teeth of the sun gear to the center of the circle of the sun gear. The wire slot is used to insert the guide wire and ensure the coaxial rotation of the guide wire. When in use, the rotation of the rotating wheel set 34 drives the concentrically connected rotating shaft 8 to rotate together, and the rotating shaft 8 drives the planet gear to rotate. The planet gear drives the sun gear 15 to rotate through the meshing effect, thereby driving the rotation of the guide wire.

The traveling assembly includes a traveling wheel set 5, a transmission screw rod 2 concentrically connected to a bevel gear of the traveling wheel set 5, and a fixed disk 10 for supporting the sun gear 15. When in use, the rotation of the bevel gear of the traveling wheel set 5 drives the transmission screw rod 2 to rotate, the fixed disk 10 is threadedly meshed with the transmission screw rod 2, and advances or retreats with the rotation of the transmission screw rod 2, and the fixed disk 10 advances or retreats to drive the guide wire advance or retreat. At least two fixed gears are provided on the fixed disk 10, and the fixed gears are meshed with the sun gear 15 for fixing the sun gear 15.

The rotating wheel set 34 and the traveling wheel set 5 are both connected to the motor(s) in the driving housing 33 through the above-mentioned magnetic induction coupling set 35, so as to be driven.

The guide wire control module 45 also includes a locking device 36 for locking the guide wire, and the locking device 36 is fixed to the sun gear 15. The locking device 36 comprises a locking control assembly, an active member, and a fixing member. The fixing member 22 is fixed to the sun gear 15 and aligned with one side of the wire slot 14. The active member is disposed relative to the fixing member and aligned with the other side of the wire slot 14. The locking control assembly is connected to the active member for controlling the positional relationship of the active member relative to the fixing member.

The locking control assembly controls the active member away from the fixed member, i.e. the wire slot 14 forms a passageway for the guide wire to be embedded, and then controls the active member against the fixed member to clamp the guide wire embedded in the wire slot 14. The locking device 36 may be an electric clamp structure, driven by electric power, or a pneumatic clamp structure, driven by pneumatic power.

The locking control assembly includes a key, a linkage rod, a spring and a limit block. The spring and the limit block are arranged in the inner cavity of the active member. The limit block is fixed. The spring is located between the limit block and the side wall of the active member. One end of the linkage rod is connected with the key, and the other end of the linkage rod is connected with the active member 21.

When the locking device 36 is in the loosened state, by pressing the key 17, the linkage rod is driven to move outward, thereby driving the active member to move radially outward and the active member is moved away from the fixed member, and at this time, the spring is in a compressed state. When the locking device 36 is in the locked state, the pressing control of the key 17 is released, and under the action of the elastic force of the spring, the active member moves radially inward and abuts against the fixed member, and the key returns to the initial position.

Preferably, the contact surface between the active member and the fixed member are toothed clamping surfaces to provide a greater clamping force to the guide wire. More preferably, the toothed clamping surfaces are coated with silicone coating.

In this Example, the positioner assembly for a vascular interventional robot includes a guide wire control module positioner and a surgical robot arm positioner.

The guide wire control module positioner is configured for the positioning of the guide wire control module 45 of the terminal execution system 54. The guide wire control module positioner includes a first sensing point 37 arranged at the bottom of the fixed disk 10, a first inductor 38 for sensing the first sensing point 37; a second sensing point 39 provided at an end of the sun gear 15 opposite to the wire slot 14, a second inductor 40 for sensing the second sensing point 39; wherein the first inductor 38 and the second inductor 40 are arranged at the bottom of the terminal execution system 54. Both the first inductor 38 and the second inductor 40 are provided on the driving housing 33, and both the first sensing point 37 and the second sensing point 39 are provided on the execution housing 32. Inductor openings 41 are provided on the execution housing 32 at positions corresponding to the first inductor 38 and the second inductor 40 on the driving housing 33. The first inductor 38 and the second inductor 40 respectively sense the first sensing point 37 and the second sensing point 39 through the inductor openings 41. Or, the bottom wall of the execution housing 32 is not provided with the inductor openings 41, the portions corresponding to the first inductor 38 and the second inductor 40 are transparent, or the bottom wall of the execution housing 32 is transparent as a whole. The first inductor 38 and the second inductor 40 of the present Example are both laser sensors.

In operation, when the first inductor 38 senses the first sensing point 37 at the bottom of the fixed disk 10 (the first sensing point 37 is directly above the first inductor 38), it sends a signal to the remote microcomputer control end 56 (e.g., computer, etc.) to axially position the guide wire control module 45. When the second inductor 40 senses a second sensing point 39 located on an end of the locking device 36 opposite the wire slot 14 (the second sensing point 39 is directly above the second inductor 40), a signal is sent to the remote microcomputer control end 56 to radially position the guide wire control module 45.

The purpose of axial positioning of the interventional device control module 45 is to facilitate calculating the advancing distance of the interventional device and setting the target position for the interventional device; the purpose of radial positioning of the interventional device control module 45 is to facilitate calculating the angle of rotation of the interventional device and setting the target angle for the interventional device.

The positioner assembly also includes a surgical robot arm positioner disposed on the driving housing 33 of the terminal execution system 54 for sensing whether the execution housing 32 is located above the driving housing 33. The surgical robot arm 55 is fixed when the surgical robot arm positioner senses that the execution housing 32 is located above the driving housing 33, and the surgical robot arm 55 is free to move when the surgical robot arm positioner senses that the execution housing 32 is removed from above the driving housing 33. The surgical robot arm positioner is an infrared sensor.

Preferably, a sterile cloth is arranged between the execution housing 32 and the driving housing 33 for blocking contamination of components in the driving housing 33 during the operation. Wherein, the parts of the sterile cloth corresponding to the inductors are transparent.

Figure 26:
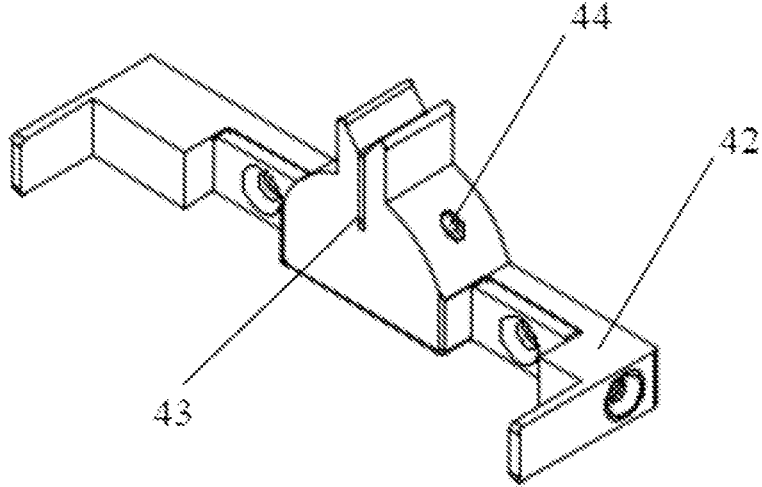
FIG. 26 is a perspective view of a sliding rod for supporting guide wire according to an example of the present invention.
Figure 27:
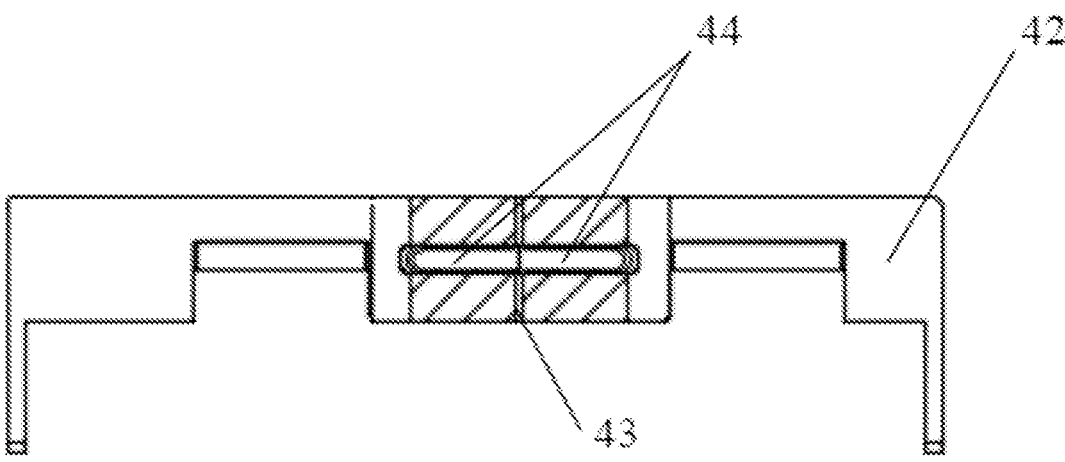
FIG. 27 is a cross-sectional view of the sliding rod for supporting guide wire in FIG. 26 to show a symmetrical round through hole.
Figure 28:
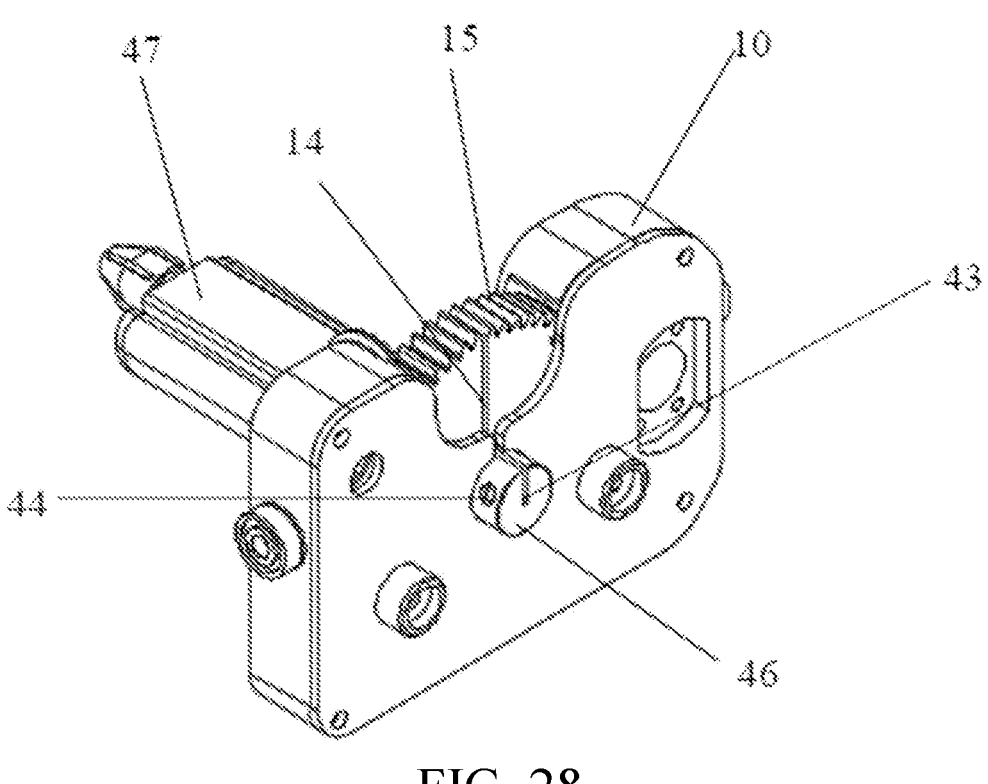
FIG. 28 is a perspective view of a guide wire center holder according to an example of the present invention.
Figure 29:
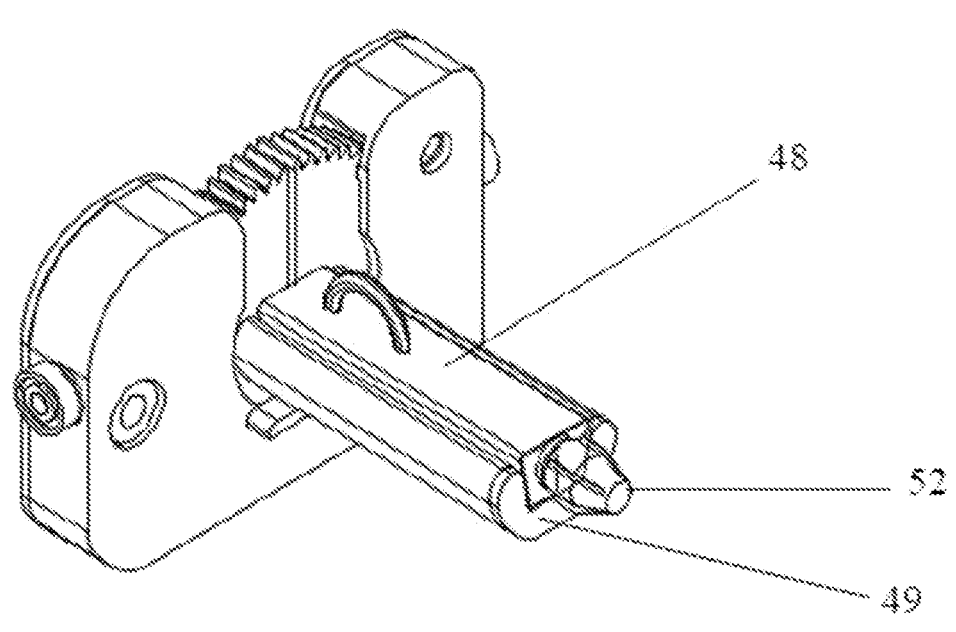
FIG. 29 is a perspective view of a guide wire locker according to an example of the present invention.
Figure 30:
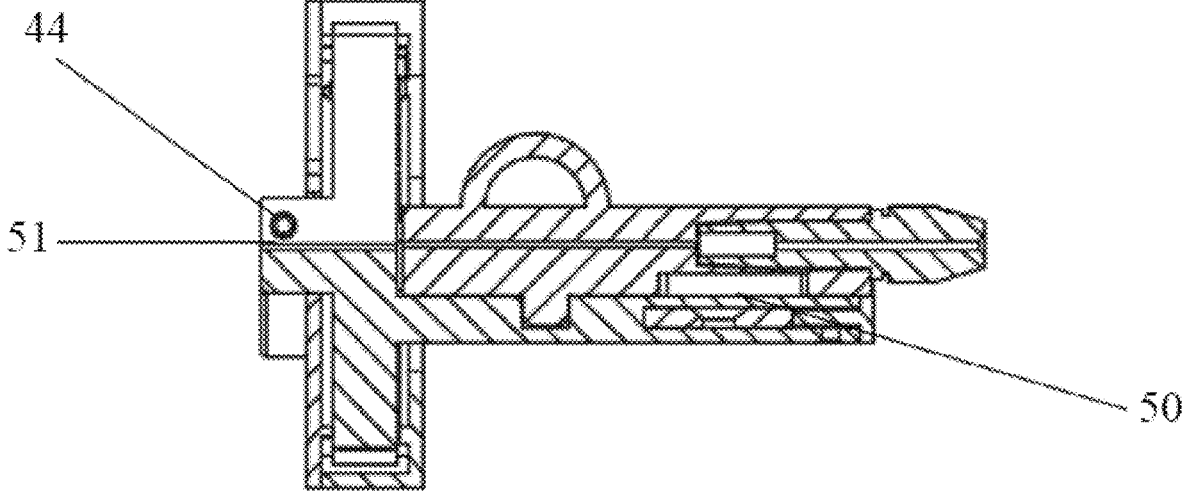
FIG. 30 is a cross-sectional view of the guide wire locker in FIG. 29.
Figures 31, 32:
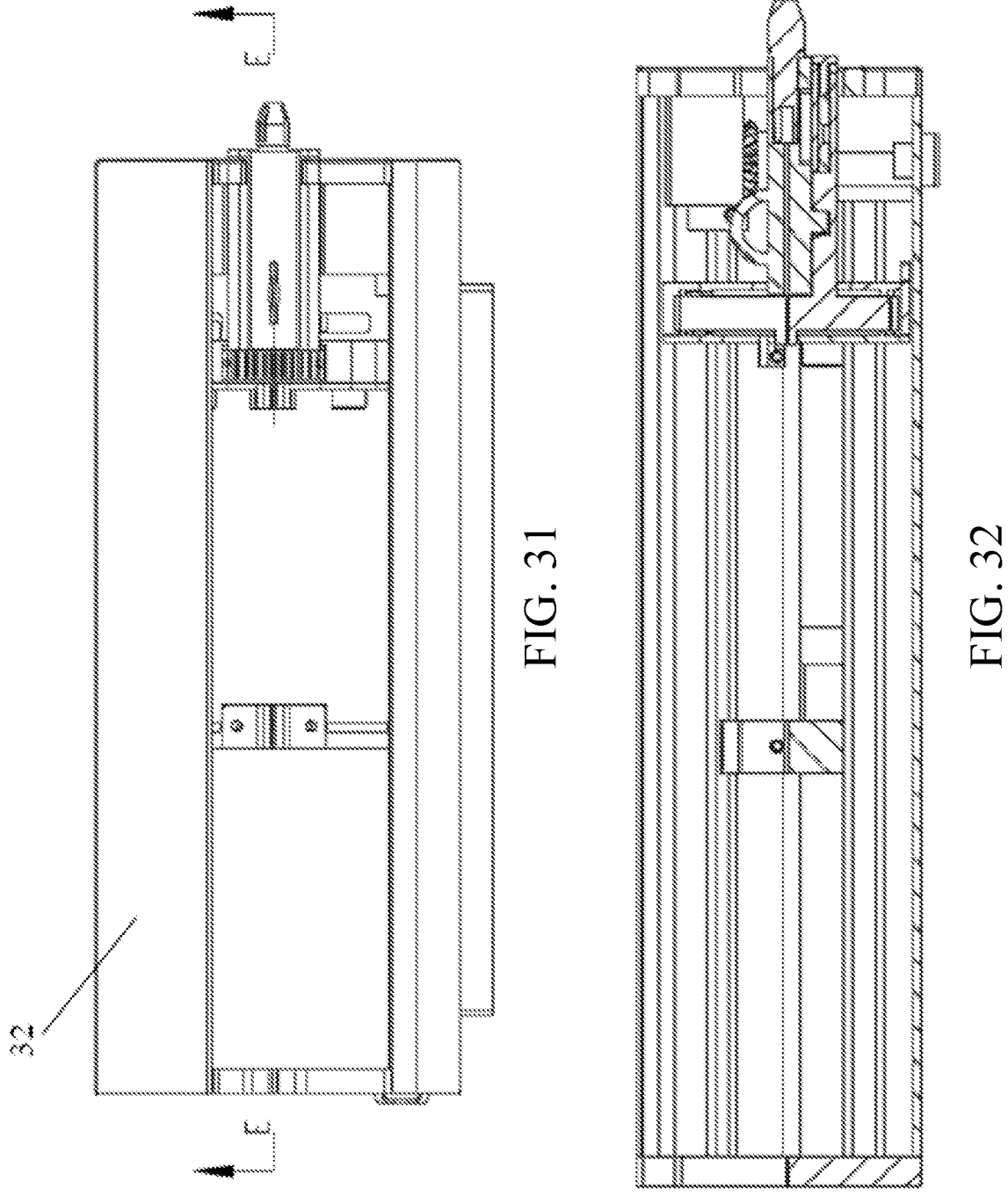
FIG. 31 is a top view of the guide wire center holder in FIG. 28 and the guide wire locker in FIG. 29 when placed in the terminal execution system.
FIG. 32 is a cross-sectional view taken along the E-E section in FIG. 31.
Figure 33:
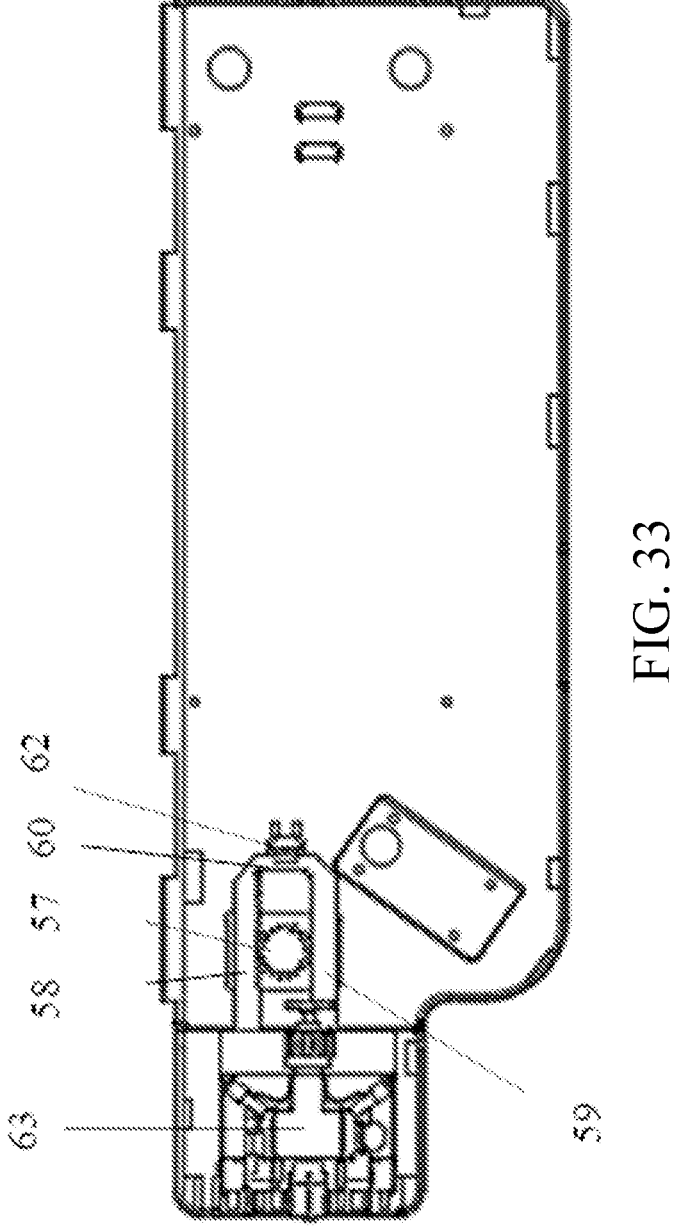
FIG. 33 is a diagram of a rack and pinion group in an initial state according to an example of the present invention.
Figure 34:
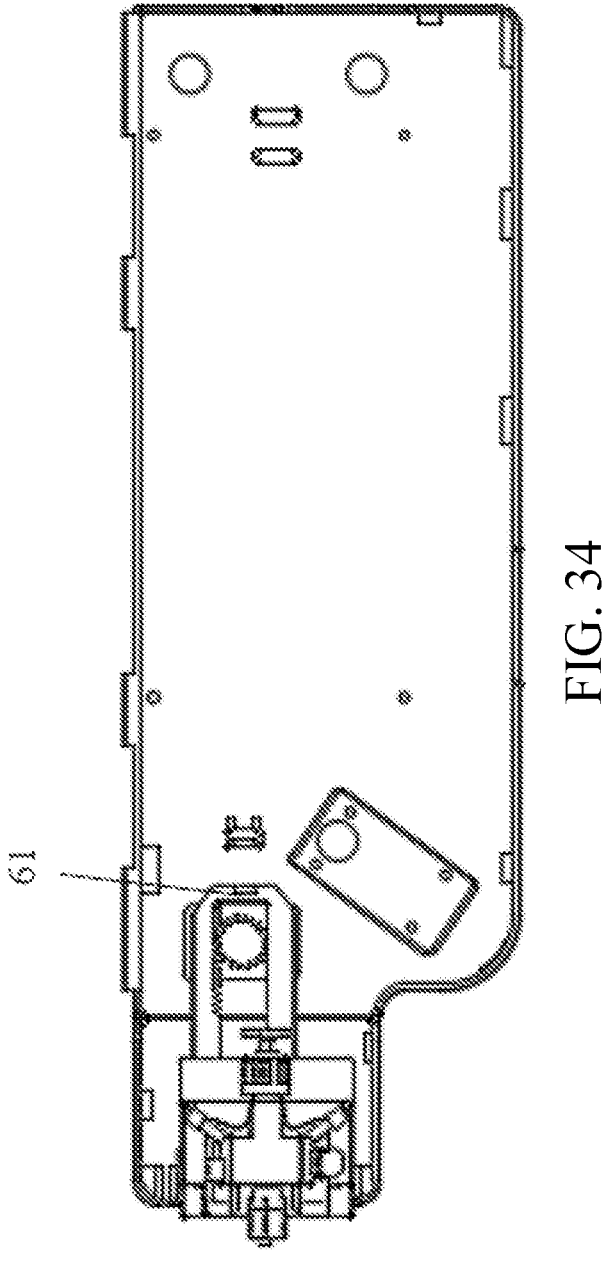
FIG. 34 is a diagram of the rack and pinion group in FIG. 33 in an operating state.
Figure 35:
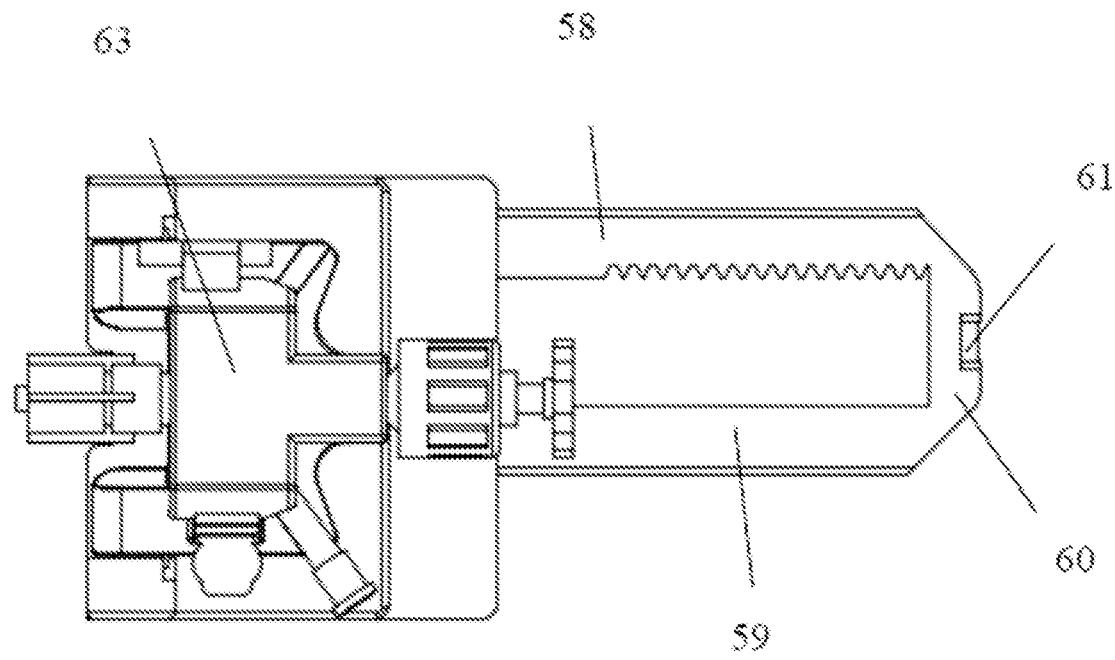
FIG. 35 is a front view of a rack frame of the rack and pinion group in FIG. 33 and FIG. 34.
Figure 36:
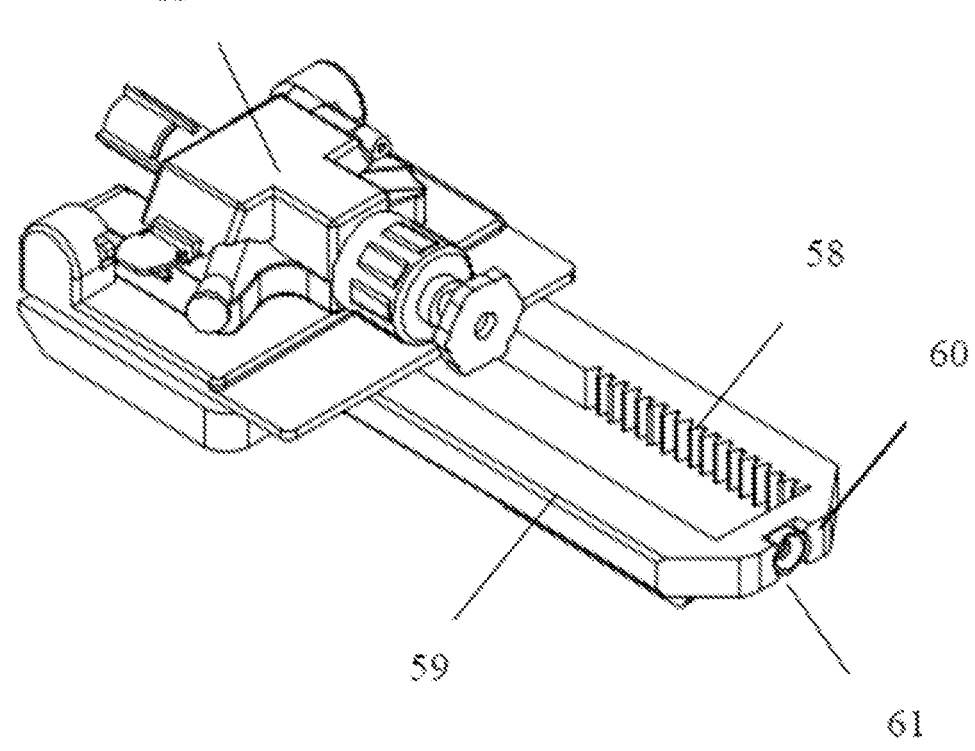
FIG. 36 is a perspective view of the rack frame of the rack and pinion group in FIG. 35.

In addition, in the guide wire control module 45 (i.e., the guide wire movement/rotation module), one end of the guide wire is clamped to the sun gear 15 and the other end rests on the housing barrel of the guide wire control module 45. At this time, a guide wire supporting sliding rod 42 is placed between the sun gear 15 and the housing cylinder. As shown in FIGS. 26-27, the guide wire supporting sliding rod 42 has a semicircular structure with two L-shaped brackets projecting from the bottom side of the semicircular bottom edge, and the two L-shaped brackets can be embedded in the sliding rail grooves on both sides of the housing cylinder, so that the guide wire supporting sliding rod 42 can move back and forth in the sliding rail grooves. The guide wire supporting sliding rod 42 is provided with an embedded groove 43 from the top to near the center of the circle, with a width of 0.1 mm to 5 mm. The height of the bottom of the embedded groove 43 is on the same horizontal line as the center of the circle of the sun gear 15 and the height of the guide wire resting point on the housing barrel of the guide wire control module 45. One round through hole 44 is respectively opened on both sides of the semicircular structure of the guide wire supporting sliding rod 42. The diameter of the round through hole 44 is 0.1 mm to 3 mm. Two flexible pipes are respectively inserted into the round through holes 44. After passing through the round through holes 44, the flexible pipes abut at the embedded groove 43 to prevent the guide wire from being warped, curled or even separated from the embedded groove 43 of the guide wire supporting sliding rod 42.

The guide wire supporting sliding rod 42 is provided with a first magnet, and correspondingly, the fixed plate 10 is provided with a second magnet, and the first magnet and the second magnet attract each other.

In the operation of conveying the guide wire, the guide wire supporting sliding rod 42 is located in the middle section between the sun gear 15 and the housing barrel and the guide wire is placed in the embedded groove 43. As the fixed disk 10 moves along the transmission screw rod 2 to the proximal end, the second magnet and the first magnet generate an attractive effect, and the guide wire supporting sliding rod 42 continues to move to the proximal end together with the fixed disk 10. In the operation of retracting the guide wire, the guide wire supporting sliding rod 42 retracts to the distal end together with the fixed disk 10. When retracts to the middle position between the sun gear 15 and the housing barrel, the guide wire supporting sliding rod 42 is fixed without retracting under the blocking action of the stop member or the walls of the slide rail grooves, while the fixed disk 10 can continue to be retracted.

Figures 40, 41:
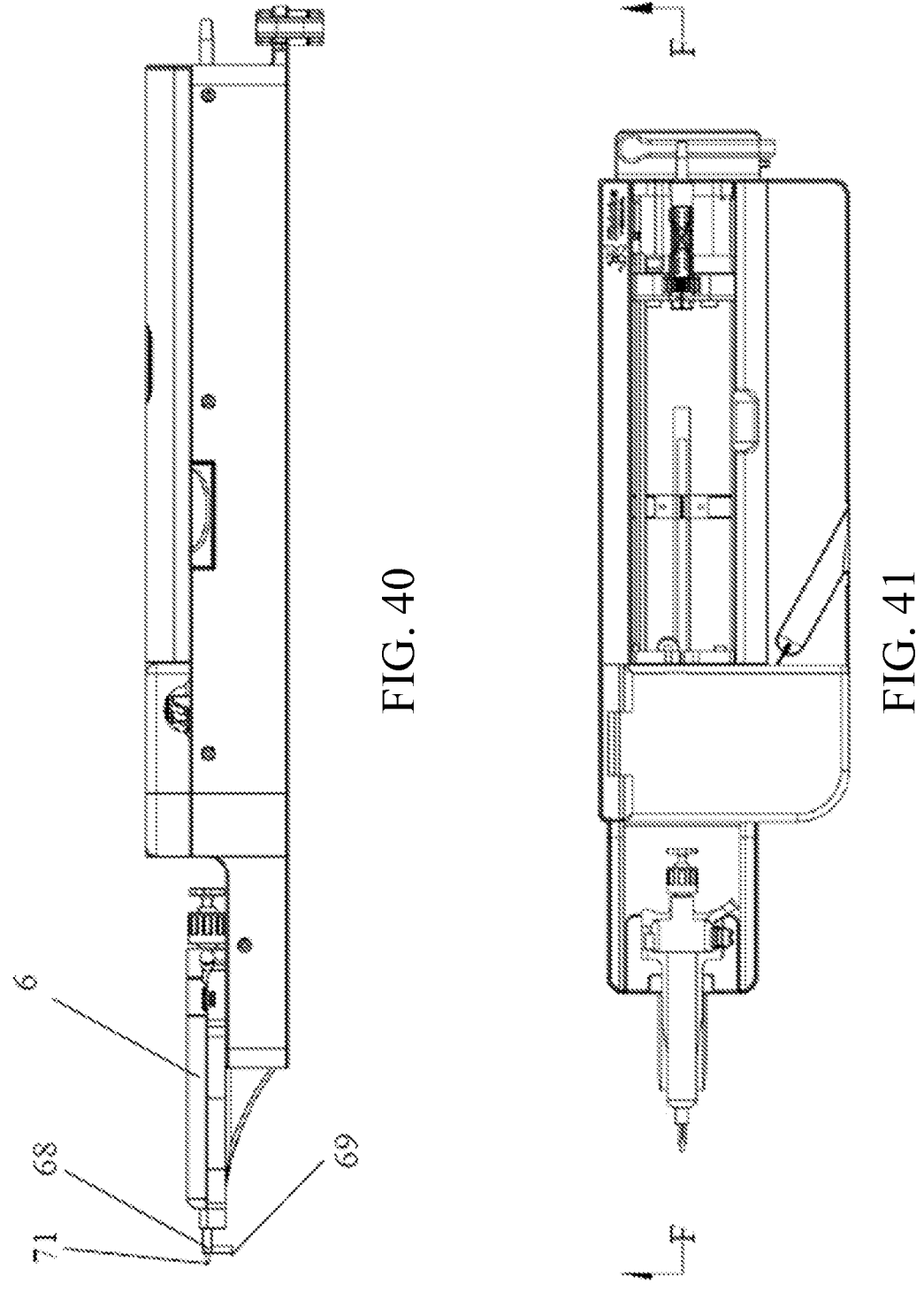
FIG. 40 is a front view of an execution housing provided with a guide catheter support component according to an example of the present invention.
FIG. 41 is a top view of the execution housing provided with the guide catheter support component according to an example of the present invention.
Figure 42:
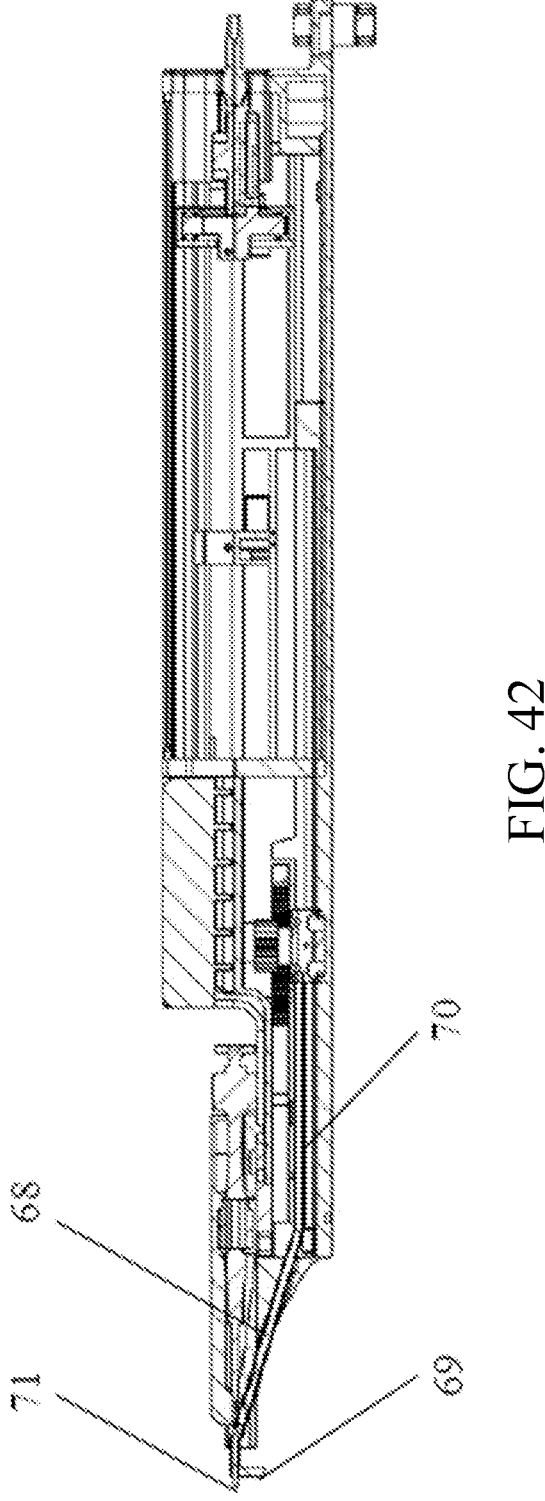
FIG. 42 is a cross-sectional view taken along the F-F section in FIG. 41.

Preferably, as shown in FIGS. 40-42, the Y-typed assembly 6 further comprises a guide catheter supporting member for supporting the guide catheter 71 extending from the Y-typed valve. The guide catheter support member includes a sliding sleeve 68, a sliding sleeve handle 69, and a sliding sleeve track 70. Wherein, a sliding sleeve track 70 is provided in the Y-typed valve for accommodating the sliding sleeve 68, and the sliding sleeve 68 can slide in the sliding sleeve track 70 to extend out of the Y-typed valve or withdraw (retracted) into the Y-typed valve. A sliding sleeve handle 69 is provided at the distal end of the sliding sleeve 68 (one end away from the operator), and the operator can control the travel of the guide catheter 71 by dragging the sliding sleeve handle 69. In one embodiment, the sliding sleeve handle 69 is a projection located at the distal end of the sliding sleeve 68. The upper part of the sliding sleeve 68 is provided with an axial slit through which the guide catheter 71 can enter and be contained within the sliding sleeve 68.

When the guide catheter 71 extends out of the Y-typed valve for a long distance, the sliding sleeve 68 is pulled out of the sliding sleeve track 70 by pulling the sliding sleeve handle 69 to support the extended guide catheter 71. If this demand does not exist, the sliding sleeve 68 is pushed back into the Y-typed valve.

Example 2

The terminal execution system 54 of the present Example is similar to the Example 1, and the difference is that the terminal execution system 54 of the present Example is further provided with a guide wire center holder 46, and the locking device 36 of the Example 1 is replaced by a guide wire locker 47, as shown in FIGS. 28-32.

The guide wire center holder 46 is provided on the sun gear 15, which has a configuration similar to the above-mentioned the embedded groove 43 and the pair of round through hole 44 of the guide wire supporting sliding rod 42. The embedded groove 43 is provided corresponding to the wire slot 14 for fixing the guide wire passing through the wire slot 14. The guide wire center holder 46 is a cylindrical structure, and is fixedly connected concentrically to the sun gear 15. The embedded groove is wire slotted to the center of the circle as in the case of the sun gear 15 and corresponds to the wire slot 14. Round through holes 44 are provided on both sides of the embedded groove for inserting flexible materials respectively. Insert the guide wire into the sun gear 15 and the limit groove, and press the guide wire with flexible materials.

A guide wire locker 47 is removably disposed on the proximal side of the sun gear 15 for locking and fixing the guide wire. The guide wire locker 47 is divided into upper and lower parts. The upper part 48 and the lower part 49 are attracted by the magnets 50 for cover closing (it should be noted that the upper part 48 and the lower part 49 can also be cover closed in other ways, including but not limited to snap-fit, nesting, bonding, friction fixing, etc.). The bottom surface of the upper part 48 and the top surface of the lower part 26 are both provided with semicircular grooves. In a state where the upper part 48 and the lower part 49 are cover closed, the two semicircular grooves are combined to form a guide wire hole 51, and a guide wire locking knob 52 is also provided at the tail end.

When operating the guide wire locker 47, remove the upper cover of the guide wire locker 47, insert the guide wire into the guide wire locking knob 52, put the guide wire into the guide wire hole 51, cover the upper and lower parts (48, 49), tighten the guide wire locking knob 52, and fix the guide wire locker 47 on the sun gear 15, so that the guide wire can rotate with the rotation of the sun gear 15.

In another embodiment, the guide wire locker 47 is a stud and nut structure, wherein the guide wire is sandwiched between the lower edge of the stud and the upper edge of the nut, the stud and the nut are tightened, and the guide wire is clamped. One of the stud and the nut is fixed to the sun gear 15.

In another embodiment, the guide wire locker 47 is a clamp structure, wherein the clamp is mounted on the sun gear 15. Loosen the clamp to put in the guide wire and clamp the clamp to clamp the guide wire.

Example 3

The terminal execution system 54 of the present Example is similar to the Example 1, and the difference is that the rack and pinion group for the guide catheter of the present Example is implemented by a single gear 57, and is positioned by a magnetic component group, as shown in FIGS. 33-36.

The robot is used for interventional therapy, including a remote microcomputer control end, a surgical positioning robot arm and a terminal execution system, wherein the terminal execution system is fixed on the end of the surgical positioning robot arm and moves with the surgical positioning robot arm, and the remote microcomputer control end controls the movement of the surgical positioning robot arm and the movement inside the terminal execution system.

The terminal execution system includes a guide catheter control module in the interventional device, the guide catheter control module is used to control the advance or retreat of the guide catheter, and the guide catheter control module includes a Y-typed assembly, which includes a Y-typed valve 63 above and a rack and pinion group below.

The distal port of the Y-typed valve 63 is connected to the guide catheter, and the proximal port is penetrated the guide wire. The guide wire enters the guide catheter through the Y-typed valve 63 and reaches the surgical site along the lumen of the guide catheter.

The rack and pinion group includes a rack frame, a single gear 57, a moving magnetic member 61 mounted on the rack frame, and a fixed magnetic member 62 interacting with the moving magnetic member 61. The Y-typed valve 63 is fixed on the rack frame and moves with the movement of the rack frame. The single gear 57 is connected to the straight rack on the rack frame by meshing. The fixed magnetic member 62 is fixed to the execution housing of the terminal execution system.

The rack frame includes a first toothed edge 58, a second straight edge 59, and a third connecting edge 60. The first toothed edge 58 is provided with a straight rack meshing with the single gear 57, and the second straight edge 59 and the first toothed edge 58 are arranged in parallel to each other. The third connecting edge 60 connects the first toothed edge 58 and the second straight edge 59 to form a semi-enclosed structure, and the single gear 57 is placed in the semi-enclosed structure. One end of the single gear 57 meshes with the straight rack of the first toothed edge 58, and the other end of the single gear 57 abuts against the second straight edge 59. The moving magnetic member 61 is fixed to the third connecting edge 60.

The rack frame interacts with the fixed magnetic member 62 fixed on the housing of the terminal execution system through the moving magnetic member 61, so as to prevent the rack frame from sliding randomly.

During the operation, the driving device drives the single gear 57 to rotate. Due to the meshing relationship between the single gear 57 and the rack frame, the rack frame overcomes the force generated by the fixed magnetic member 62 and moves forward, thereby driving the Y-typed valve 63 to move forward, thus avoiding the loss of accuracy due to unwanted relative displacement between the parts.

The driving device is a non-contact motor system. The non-contact motor system includes a motor, a first magnetic induction coupling coupled to the motor and driven by the motor, a second magnetic induction coupling corresponding to the first magnetic induction coupling, and a transmission gear set coupled to the second magnetic induction coupling. The first magnetic induction coupling and the second magnetic induction coupling are coaxially opposed. A distance between the first magnetic induction coupling and the second magnetic induction coupling is in the range of 2 mm to 20 mm.

Example 4

Figure 37:
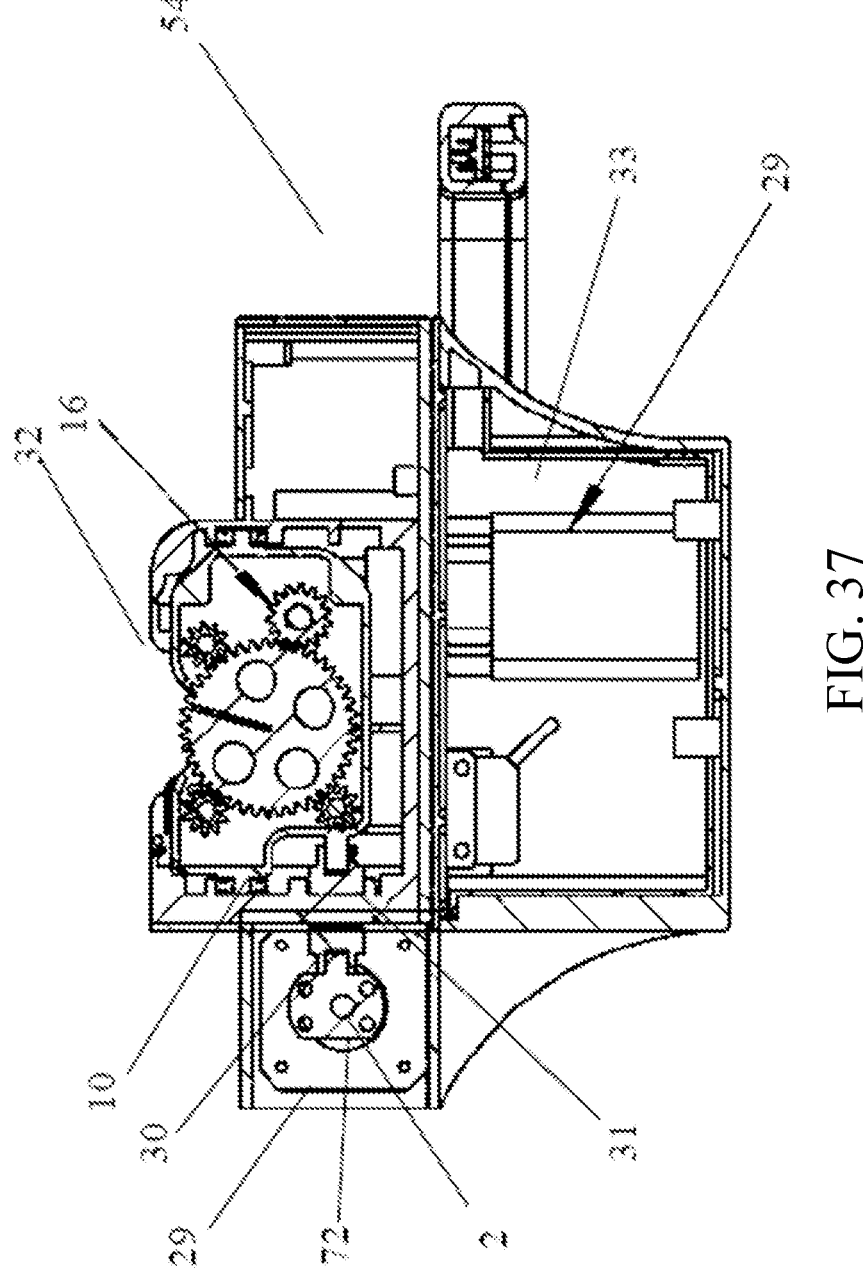
FIG. 37 is a cross-sectional view of a terminal execution system according to another example of the present invention.

The terminal execution system 54 of this Example is similar to the Example 1, and the differences are that the second magnetic induction coupling 31 is directly connected to the fixed disk 10, the transmission screw rod 2 and the motor 29 that drives the transmission screw rod 2 to rotate are moved to the side of the terminal execution system 54, the motor shaft of the motor 29 is directly connected to the shaft of the transmission screw rod 2, the motor 29 drives the transmission screw rod 2 to rotate, and an intermediate connector 72 is added to be sleeved on the transmission screw rod 2 and be threaded to the transmission screw rod 2. With the rotation of the transmission screw rod 2, the intermediate connector 72 can move back and forth. The first magnetic induction coupling 30 is fixedly connected with the intermediate connector 72, the second magnetic induction coupling 31 is also oriented to the side in conjunction with the first magnetic induction coupling 30, which is coupled to the intermediate connector 72 located on the side, under magnetic force. These constitute a new wheel set traveling mechanism that allows the wheel set 3 to move forward and backward while the motor 29 is rotating, as shown in FIG. 37.

Example 5

Figure 38:
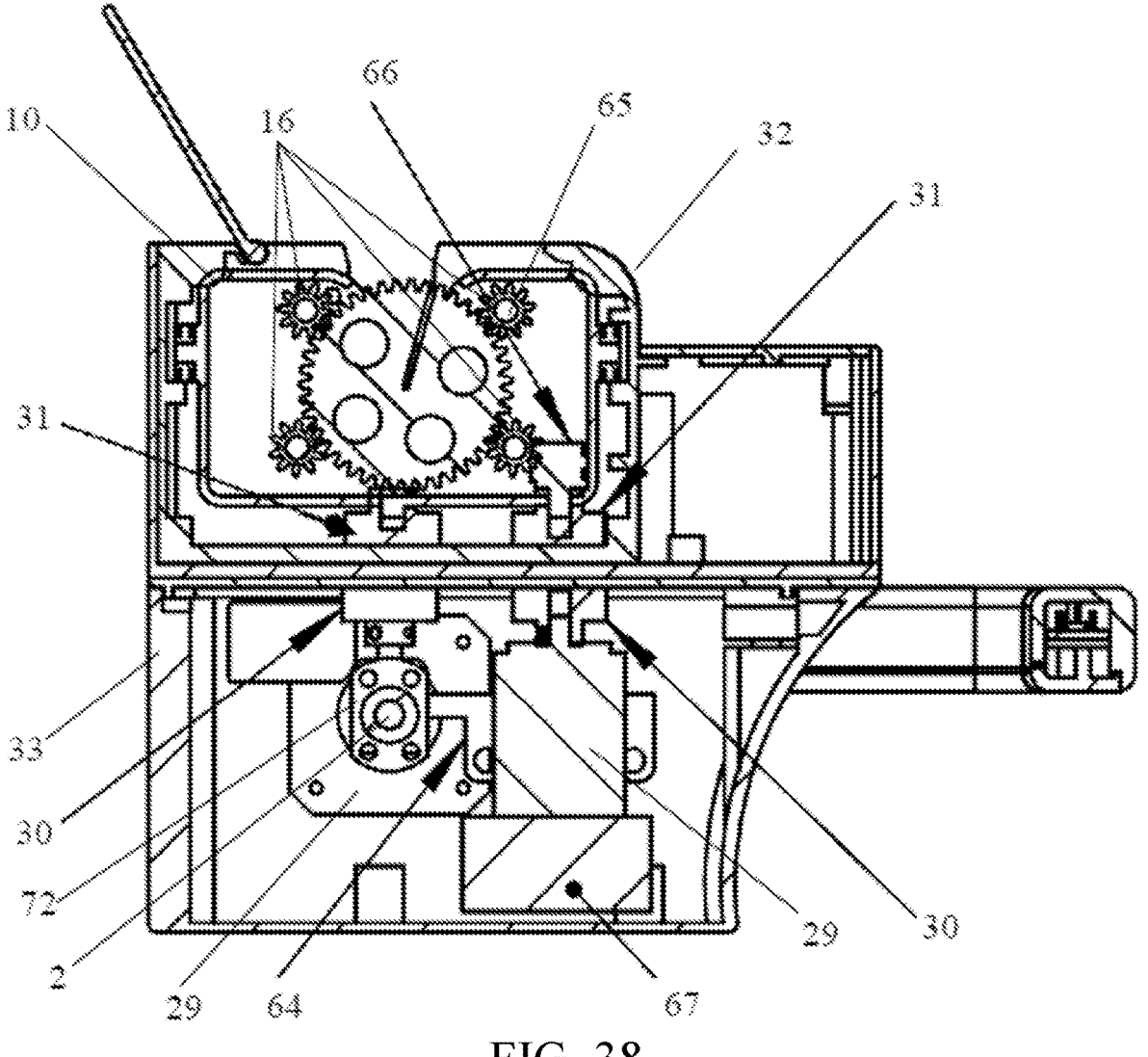
FIG. 38 is a cross-sectional view of the terminal execution system according to yet another example of the present invention.
Figure 39:
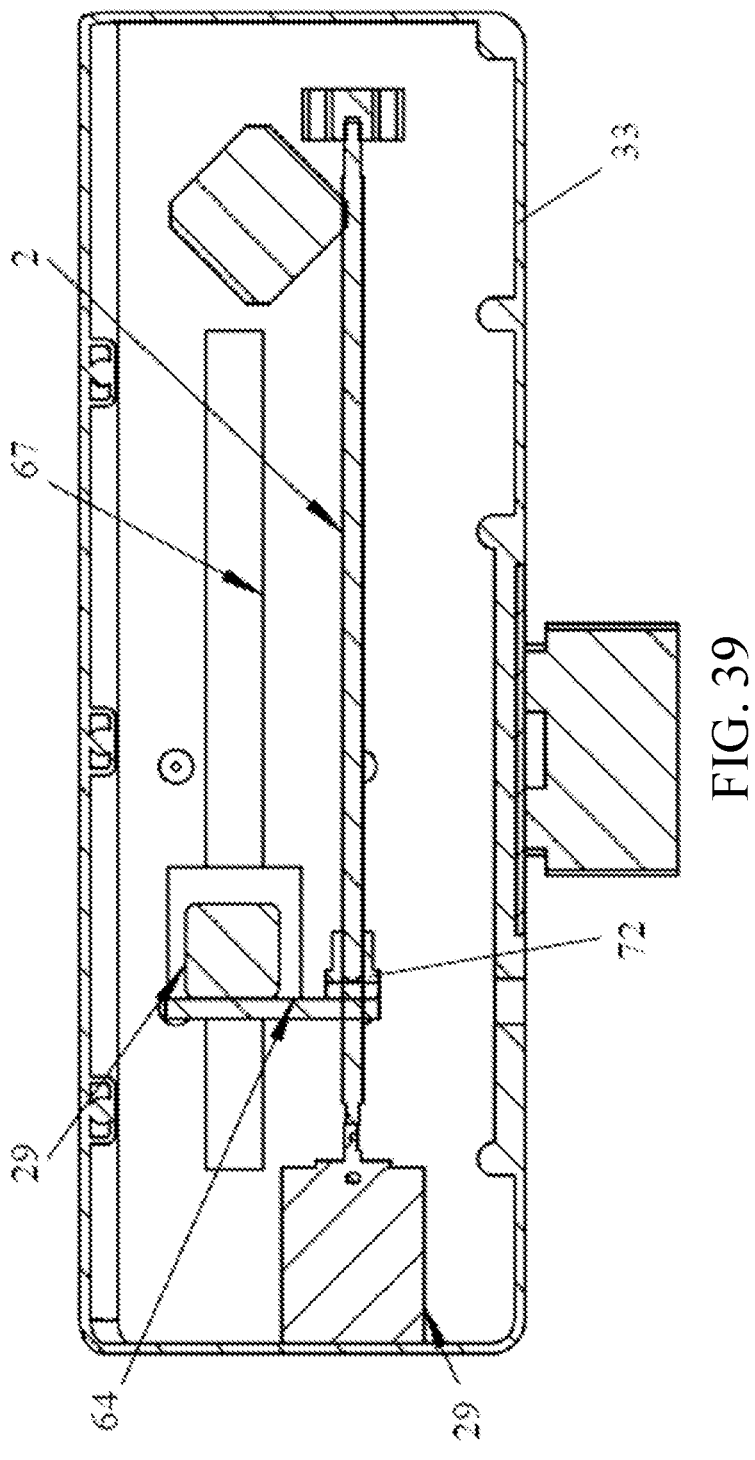
FIG. 39 is an axial cross-sectional view of the terminal execution system according to another example of the present invention.

As shown in FIGS. 38-39, the terminal execution system 54 of this Example is similar to Example 4, and the differences are that the transmission screw rod 2 and the motor 29 that drives the transmission screw rod 2 to rotate are moved to the driving housing 33 in this Example, and the first magnetic induction coupling 30 and the second magnetic induction coupling 31 form an up-down matching relationship. In addition, the motor 29 driving the rotation of the planet gear 16 is also moved into the driving housing 33, and the rotating shaft 8 is eliminated. Instead, the motor 29 driving the rotation of the planet gear 16 is attached to the intermediate connector 72 (e.g., via a tray 64 in FIG. 38) and travels in sync with the wheel set 3 as the transmission screw rod 2 rotates. Correspondingly, in the execution housing 32, the planet gears 16 are fixed in the fixed disk 10 through smooth axes 65, and the planet gear 16 is rotatable relative to the smooth axis 65, one of the planet gears 16 (e.g., the planet gear located in the lower right corner in FIG. 38) is engaged with the second magnetic induction coupling 31 through a worm 66, a transmission gear (group), etc.

When the motor 29 drives the transmission screw rod 2 to rotate, the wheel set 3 is driven by an intermediate connector 72 and the magnetic induction coupling set, and at the same time, with the rotation of the transmission screw rod 2, the motor 29 that drives the planet gear 16 to rotate and the wheel set 3 travel synchronously, and the motor 29 that drives the planet gear 16 to rotate drives the planet gear 16 in the fixed disk 10 to rotate through another magnetic induction coupling set, in turn, the sun gear 15 engaged with the planet wheel 16 is caused to rotate.

Preferably, a support guide rail 67 is provided below the motor 29 that drives the planet wheels 16 to rotate, for supporting and guiding the motor 29 that drives the planet wheels 16 to rotate. In a preferred embodiment, the support guide rail 67 comprises a guide rail disposed on the driving housing 33 and a roller attached below the motor 29 that drives the rotation of the planet wheel 16, wherein the roller can slide in the guide rail so as to play a supporting and guiding role. In another preferred embodiment, the support guide rail 67 is a smooth-surfaced guide strip disposed on the driving housing 33, the upper surface of the guide strip is in sliding contact with the lower surface of the motor 29 that drives the rotation of the planet wheels 16 (or by means of magnetic suspension support guide, etc.) to provide support and guidance. The above-described embodiments of the support guide rail 67 is not meant to be limited, and it may have other various embodiments as long as it can be realized to provide guidance and support for the motor 29 that drives the rotation of the planet wheel 16.

All documents mentioned in the present invention are cited by reference in this application, just as each document is cited separately as a reference. In addition, it should be understood that after reading the above teachings of the present invention, those skilled in the art can make various changes or modifications to the present invention, and these equivalent forms also fall within the scope defined by the appended claims of this application.

The invention claimed is:

1. A surgical robot system for assisted positioning (i.e. navigation) in vascular interventions, characterized in that, the system comprises a remote microcomputer control end, a surgical positioning robot arm and a terminal execution system, wherein the terminal execution system comprises a guide wire control module configured to control advance, retreat and rotation of a guide wire, comprising:

a rotating assembly configured to control the rotation of the guide wire, the rotating assembly including a rotating wheel set, a rotating shaft concentrically connected to the rotating wheel set, a planet gear sleeved on the rotating shaft and slidable relative to the rotating shaft, and a sun gear meshing with the planet gear, wherein the sun gear is provided with a wire slot, which opens from a valley between teeth of the sun gear to center of the sun gear, and is structured to insert the guide wire and ensure coaxial rotation of the guide wire, an opening of the wire slot is located at bottom of the valley between adjacent teeth of the sun gear, which does not affect the meshing between the sun gear and other gears, wherein the rotation of the rotating wheel set in the guide wire control module drives a concentrically connected rotating shaft to rotate together, and the rotating shaft drives the planet gear to rotate, the planet gear drives the sun gear to rotate through meshing effect, thereby driving the rotation of the guide wire;

a locking device for locking the guide wire, and the locking device is fixed on the sun gear, and a traveling component configured to control the advance or retreat of the guide wire, the traveling component including a traveling wheel set, a transmission screw concentrically connected with a bevel gear of the traveling wheel set, and a fixed disk for supporting the sun gear, wherein rotation of the bevel gear of the traveling wheel set drives a transmission screw rod to rotate, the fixed disk is threadedly meshed with the transmission screw rod, and advances or retreats with rotation of the transmission screw rod, and an advance or retreat of the fixed disk drives the guide wire advance or retreat;

a balloon/stent control module configured to control advance or retreat of a balloon catheter or a stent catheter, the balloon/stent control module including a transmission wheel assembly comprising a friction wheel set, wherein there are friction wheel set gears meshing with each other under the friction wheel set, and the friction wheel set clamps the balloon catheter or the stent catheter to move it advance or retreat; and a guide catheter control module configured to control advance or retreat of the guide catheter, the guide catheter control module including a Y-typed assembly, the Y-typed assembly comprising an upper Y-typed valve and a lower rack and pinion group, wherein a distal port of the Y-typed valve is connected to the guide catheter, a proximal port is penetrated the guide wire, the guide wire enters the guide catheter through the Y-typed valve and reaches a surgical site along lumen of the guide catheter, and the rack and pinion group drives the Y-typed assembly forward or backward, thereby driving the guide catheter forward or backward;

wherein, the rotating wheel set, the traveling wheel set, the friction wheel set and the Y-typed assembly are all driven by motors and connected with a remote microcomputer;

wherein in longitudinal direction of an entire system, a plurality of wire slots are provided from a proximal end to a distal end, which can directly place the guide wire from top to bottom, including an outer box, a wheel set, a pulley and a fixed plate, so as to facilitate a placement of the guide wire before the surgery and a removal and exchange of the guide wire during the surgery, and also facilitate the cooperation of the guide wire and the balloon catheter or stent catheter.

2. The system according to claim 1, wherein gears of the friction wheel set of the transmission wheel assembly in the balloon/stent control module rotates to drive the friction wheels above to rotate, and rotation of the friction wheels drives forward or backward movement of the balloon catheter or stent catheter clamped by the friction wheels.

3. The system according to claim 1, wherein a gear(s) in the rack and pinion group of the Y-typed assembly in the guide catheter module drives a rack(s) meshed therewith to move, so that the Y-typed valve and the guide catheter connected thereto advance or retreat.

4. The system according to claim 1, wherein at least two fixed gears are provided on the fixed disk, and the fixed gears are meshed and connected with the sun gear for fixing the sun gear.

5. The system according to claim 1, wherein the locking device comprises a locking control assembly, an active member and a fixed member, the fixed member is fixed to the sun gear and aligned with one side of the wire slot, the active member is provided opposite to the fixed member and aligned with the other side of the wire slot, and the locking control assembly is connected to the active member for controlling a positional relationship of the active member relative to the fixed member;

the locking control assembly includes a key, a linkage rod, a spring and a limit block, the spring and the limit block are provided in an inner cavity of the active member, the limit block is fixed, the spring is located between the limit block and a side wall of the active member, one end of the linkage rod is connected with the key, and the other end is connected with the active member.

6. The system according to claim 1, wherein an operator remotely controls movement of the guide wire control module, the balloon/stent control module, and the guide catheter control module via the remote microcomputer control end using signal transmission.

7. The system according to claim 1, wherein the system comprises a non-contact motor system, and the non-contact motor system is arranged on the terminal execution system for providing a drive force for forward, backward and rotational movement of an interventional device;

the non-contact motor system includes a motor, a first magnetic induction coupling coupled to the motor and driven by the motor, a second magnetic induction coupling provided opposite to the first magnetic induction coupling, and a transmission structure coupled to the second magnetic induction coupling; wherein the first magnetic induction coupling and the second magnetic induction coupling are coaxially opposed; and a distance between the first magnetic induction coupling and the second magnetic induction coupling is in a range of 0 mm to 20 mm.

8. The system according to claim 1, wherein the rack and pinion group comprises a rack frame, and the Y-typed valve is fixed on the rack frame; a gear meshed with a straight rack on the rack frame; a moving magnetic member installed on the rack frame; and a fixed magnetic member interacting with the moving magnetic member; wherein the fixed magnetic member is fixed on a housing of the terminal execution system.

9. The system according to claim 1, wherein the system comprises a locator assembly, the locator assembly comprises a guide wire control module locator, and the guide wire control module locator is used for positioning of the guide wire control module of the terminal execution system;

the guide wire control module positioner includes a first sensing point provided at a bottom of the fixed disk, a first inductor for sensing the first sensing point; a second sensing point provided at an end of the sun gear opposite to the wire slot, a second inductor for sensing the second sensing point; the first inductor and the second inductor are provided at a bottom of the terminal execution system;

wherein the first inductor determines a position of the fixed disk by sensing the first sensing point, and in the case of determining the position of the fixed disk, the second sensor determines an angular position of the sun gear by sensing the second sensing point.

* * * * *